US012653435B2

(12) United States Patent (10) Patent No.: US 12,653,435 B2
Bishay et al. (45) **Date of Patent: \*Jun. 16, 2026**

(54) ELECTROCARDIOGRAPHY PATCH

(71) Applicant: Bardy Diagnostics, Inc., Bellevue, WA (US)

(72) Inventors: Jon Mikalson Bishay, Seattle, WA (US); Gust H. Bardy, Carnation, WA (US); Jason Felix, Vashon Island, WA (US)

(73) Assignee: Bardy Diagnostics, Inc., Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/328,571

(22) Filed: Jun. 2, 2023

(65) Prior Publication Data

US 2023/0309893 A1 Oct. 5, 2023

Related U.S. Application Data

(63) Continuation of application No. 17/121,700, filed on Dec. 14, 2020, now Pat. No. 11,701,044, which is a
(Continued)

(51) Int. Cl.
*A61B 5/00* (2006.01)
*A61B 5/0205* (2006.01)
(Continued)

(52) U.S. Cl.
CPC ............ *A61B 5/282* (2021.01); *A61B 5/0006* (2013.01); *A61B 5/0022* (2013.01);
(Continued)

(58) Field of Classification Search
CPC .................. A61B 5/282; A61B 5/0006; A61B 2560/0412; A61B 5/6833; A61B 5/259;
(Continued)

(56) References Cited

U.S. PATENT DOCUMENTS 3,215,136 A 11/1965 Holter et al.
3,569,852 A 3/1971 Berkovits
(Continued)

FOREIGN PATENT DOCUMENTS

CA 2535502 3/2005
CA 2651203 8/2007
(Continued)

OTHER PUBLICATIONS

US 6,527,714 B2, 03/2003, Bardy (withdrawn)
(Continued)

*Primary Examiner* — Joseph A Stoklosa
*Assistant Examiner* — Brian M Antiskay
(74) *Attorney, Agent, or Firm* — K&L Gates LLP

(57) ABSTRACT

An electrocardiography patch is provided. A backing has an elongated strip with a midsection connecting two rounded ends. The midsection tapers in from each of the rounded ends and is narrower than each of the two rounded ends. Each electrode, of a pair of electrodes, is positioned on one of the rounded ends of the backing, on a contact surface, to capture electrocardiographic signals. A flex circuit is coupled to each of the electrodes. A non-conductive receptacle is affixed on an outer surface of the backing, opposite the contact surface. Electrical contacts are provided on a surface of the non-conductive receptacle opposite the backing. A battery is provided on the outer surface of the backing and a processor is powered by the battery to write the electrocardiographic signals into memory.

17 Claims, 4 Drawing Sheets

Related U.S. Application Data continuation of application No. 15/905,715, filed on Feb. 26, 2018, now Pat. No. 11,103,173, which is a continuation of application No. 15/406,627, filed on Jan. 13, 2017, now Pat. No. 9,901,274, which is a continuation of application No. 14/080,717, filed on Nov. 14, 2013, now Pat. No. 9,545,204.

(60) Provisional application No. 61/882,403, filed on Sep. 25, 2013.

(51) Int. Cl.

| | |
|---|---|
| *A61B 5/05* | (2021.01) |
| *A61B 5/11* | (2006.01) |
| *A61B 5/259* | (2021.01) |
| *A61B 5/282* | (2021.01) |
| *A61B 5/316* | (2021.01) |
| *A61B 5/335* | (2021.01) |
| *A61B 5/349* | (2021.01) |
| *A61B 5/35* | (2021.01) |
| *A61B 5/01* | (2006.01) |
| *A61B 5/021* | (2006.01) |
| *A61B 5/08* | (2006.01) |
| *A61B 5/087* | (2006.01) |
| *A61B 5/091* | (2006.01) |
| *A61B 5/145* | (2006.01) |
| *A61B 5/1455* | (2006.01) |
| *G01N 27/30* | (2006.01) |

(52) U.S. Cl.
CPC ........ *A61B 5/02055* (2013.01); *A61B 5/1116* (2013.01); *A61B 5/1117* (2013.01); *A61B 5/1118* (2013.01); *A61B 5/259* (2021.01); *A61B 5/316* (2021.01); *A61B 5/335* (2021.01); *A61B 5/349* (2021.01); *A61B 5/35* (2021.01); *A61B 5/4809* (2013.01); *A61B 5/6801* (2013.01); *A61B 5/6823* (2013.01); *A61B 5/6833* (2013.01); *A61B 5/01* (2013.01); *A61B 5/021* (2013.01); *A61B 5/0816* (2013.01); *A61B 5/087* (2013.01); *A61B 5/091* (2013.01); *A61B 5/14532* (2013.01); *A61B 5/14542* (2013.01); *A61B 5/14551* (2013.01); *A61B 5/7455* (2013.01); *A61B 2505/07* (2013.01); *A61B 2560/0271* (2013.01); *A61B 2560/0412* (2013.01); *A61B 2560/045* (2013.01); *A61B 2562/0219* (2013.01); *A61B 2562/164* (2013.01); *G01N 27/307* (2013.01)

(58) Field of Classification Search
CPC ....... A61B 5/28; A61B 5/1118; A61B 5/1117; A61B 2560/0468; A61B 5/02405; A61B 5/256; A61B 5/6804
USPC ....... 600/372, 382, 384, 386, 388, 390–393, 600/508–509
See application file for complete search history.

(56) References Cited

U.S. PATENT DOCUMENTS

| | | | |
|---|---|---|---|
| 3,602,215 A | 8/1971 | Parnell |
| 3,699,948 A | 10/1972 | Ota et al. |
| 3,718,772 A | 2/1973 | Sanctuary |
| 3,893,453 A | 7/1975 | Goldberg |
| 3,943,918 A | 3/1976 | Lewis |
| 3,986,495 A | 10/1976 | Miller |
| 3,993,049 A | 11/1976 | Kater |
| 4,123,785 A | 10/1978 | Cherry et al. |
| 4,151,513 A | 4/1979 | Menken et al. |
| 4,280,507 A | 7/1981 | Rosenberg |
| 4,328,814 A | 5/1982 | Arkans |
| 4,365,634 A | 12/1982 | Bare et al. |
| 4,441,500 A | 4/1984 | Sessions et al. |
| 4,506,678 A | 3/1985 | Russell et al. |
| 4,532,934 A | 8/1985 | Kelen |
| 4,546,342 A | 10/1985 | Weaver et al. |
| 4,550,502 A | 11/1985 | Grayzel |
| 4,559,953 A | 12/1985 | Wright et al. |
| 4,580,572 A | 4/1986 | Granek et al. |
| 4,635,646 A | 1/1987 | Gilles et al. |
| 4,653,022 A | 3/1987 | Koro |
| 4,716,903 A | 1/1988 | Hansen |
| 4,763,660 A | 8/1988 | Kroll et al. |
| 4,788,983 A | 12/1988 | Brink et al. |
| 4,795,516 A | 1/1989 | Strand |
| 4,809,705 A | 3/1989 | Ascher |
| 4,915,656 A | 4/1990 | Alferness |
| 4,951,672 A | 8/1990 | Buchwald et al. |
| 5,007,429 A | 4/1991 | Treatch et al. |
| 5,010,888 A | 4/1991 | Jadvar et al. |
| 5,025,794 A | 6/1991 | Albert et al. |
| 5,038,782 A | 8/1991 | Gevins et al. |
| 5,093,036 A | 3/1992 | Shafe et al. |
| 5,107,480 A | 4/1992 | Naus |
| 5,168,876 A | 12/1992 | Quedens et al. |
| 5,169,679 A | 12/1992 | Palanisamy |
| 5,195,523 A | 3/1993 | Cartmell et al. |
| 5,215,098 A | 6/1993 | Steinhaus |
| 5,231,990 A | 8/1993 | Gauglitz |
| D341,423 S | 11/1993 | Bible |
| 5,263,481 A | 11/1993 | Axelgaard |
| 5,265,579 A | 11/1993 | Ferrari |
| 5,312,446 A | 5/1994 | Holschbach et al. |
| 5,314,453 A | 5/1994 | Jeutter |
| 5,331,966 A | 7/1994 | Bennett et al. |
| 5,333,615 A | 8/1994 | Craelius et al. |
| 5,337,748 A | 8/1994 | McAdams et al. |
| 5,341,806 A | 8/1994 | Gadsby et al. |
| 5,348,008 A | 9/1994 | Bomn et al. |
| 5,355,891 A | 10/1994 | Wateridge et al. |
| 5,365,934 A | 11/1994 | Leon et al. |
| 5,365,935 A | 11/1994 | Righter et al. |
| 5,392,784 A | 2/1995 | Gudaitis |
| 5,397,284 A | 3/1995 | Matsumoto et al. |
| D357,069 S | 4/1995 | Plahn et al. |
| 5,402,780 A | 4/1995 | Faasse, Jr. |
| 5,402,884 A | 4/1995 | Gilman et al. |
| 5,450,845 A | 9/1995 | Axelgaard |
| 5,451,876 A | 9/1995 | Sendford et al. |
| 5,458,141 A | 10/1995 | Neil |
| 5,473,537 A | 12/1995 | Glazer et al. |
| 5,479,922 A | 1/1996 | Reichl |
| 5,483,969 A | 1/1996 | Testerman et al. |
| 5,511,553 A | 4/1996 | Segalowitz |
| 5,540,733 A | 7/1996 | Testerman et al. |
| 5,546,952 A | 8/1996 | Erickson |
| 5,549,655 A | 8/1996 | Erickson |
| 5,579,919 A | 12/1996 | Gilman et al. |
| 5,582,181 A | 12/1996 | Ruess |
| D377,983 S | 2/1997 | Sabri et al. |
| 5,601,089 A | 2/1997 | Bledsoe et al. |
| 5,623,935 A | 4/1997 | Faisandier |
| 5,665,477 A | 9/1997 | Meathrel et al. |
| 5,676,559 A | 10/1997 | Laub et al. |
| 5,682,901 A | 11/1997 | Kamen |
| 5,697,955 A | 12/1997 | Stolte |
| 5,709,927 A | 1/1998 | Miyase et al. |
| 5,717,151 A | 2/1998 | Straubinger |
| 5,724,967 A | 3/1998 | Venkatachalam |
| 5,749,902 A | 5/1998 | Olsen et al. |
| 5,788,633 A | 8/1998 | Mahoney |
| 5,817,151 A | 10/1998 | Olson et al. |
| 5,819,741 A | 10/1998 | Karlsson et al. |
| 5,850,920 A | 12/1998 | Gilman et al. |
| 5,860,918 A | 1/1999 | Schradi et al. |
| 5,862,803 A | 1/1999 | Besson et al. |
| D407,159 S | 3/1999 | Roberg |
| 5,876,351 A | 3/1999 | Rohde |

(56)                References Cited

U.S. PATENT DOCUMENTS

| | | | |
|---|---|---|---|
| 5,906,583 | A | 5/1999 | Rogel |
| 5,913,829 | A | 6/1999 | Reeves et al. |
| 5,919,155 | A | 7/1999 | Lattin et al. |
| 5,944,662 | A | 8/1999 | Schoendorfer |
| 5,951,598 | A | 9/1999 | Bishay et al. |
| 5,956,013 | A | 9/1999 | Raj et al. |
| 5,957,857 | A | 9/1999 | Hartley |
| 5,984,102 | A | 11/1999 | Tay |
| 5,987,352 | A | 11/1999 | Klein et al. |
| 5,995,861 | A | 11/1999 | Price |
| 6,032,064 | A | 2/2000 | Devlin et al. |
| 6,038,469 | A | 3/2000 | Karlsson et al. |
| 6,101,413 | A | 8/2000 | Olsen et al. |
| 6,115,638 | A | 9/2000 | Groenke |
| 6,117,077 | A | 9/2000 | Del Mar et al. |
| 6,134,479 | A | 10/2000 | Brewer et al. |
| 6,148,233 | A | 11/2000 | Owen et al. |
| 6,149,602 | A | 11/2000 | Arcelus |
| 6,149,781 | A | 11/2000 | Forand |
| 6,185,452 | B1 | 2/2001 | Schulman et al. |
| 6,188,407 | B1 | 2/2001 | Smith et al. |
| 6,223,080 | B1 | 4/2001 | Thompson |
| D443,063 | S | 5/2001 | Pisani et al. |
| 6,229,098 | B1 | 5/2001 | Dunn et al. |
| 6,238,338 | B1 | 5/2001 | DeLuca et al. |
| 6,245,025 | B1 | 6/2001 | Torok et al. |
| 6,246,330 | B1 | 6/2001 | Nielsen |
| 6,249,696 | B1 | 6/2001 | Olson et al. |
| D445,507 | S | 7/2001 | Pisani et al. |
| 6,267,723 | B1 | 7/2001 | Matsumura et al. |
| 6,269,267 | B1 | 7/2001 | Bardy et al. |
| 6,272,385 | B1 | 8/2001 | Bishay et al. |
| 6,289,238 | B1 | 9/2001 | Besson et al. |
| 6,298,255 | B1 | 10/2001 | Cordero et al. |
| 6,301,502 | B1 | 10/2001 | Owen et al. |
| 6,304,773 | B1 | 10/2001 | Taylor et al. |
| 6,304,780 | B1 | 10/2001 | Owen et al. |
| 6,304,783 | B1 | 10/2001 | Lyster et al. |
| 6,322,532 | B1 | 11/2001 | D'Sa et al. |
| 6,341,230 | B1 | 1/2002 | Koike et al. |
| 6,374,138 | B1 | 4/2002 | Owen et al. |
| 6,381,482 | B1 | 4/2002 | Jayaraman et al. |
| 6,416,471 | B1 | 7/2002 | Kumar et al. |
| 6,418,342 | B1 | 7/2002 | Owen et al. |
| 6,424,860 | B1 | 7/2002 | Karlsson et al. |
| 6,427,083 | B1 | 7/2002 | Owen et al. |
| 6,427,085 | B1 | 7/2002 | Boon et al. |
| 6,434,410 | B1 | 8/2002 | Cordero |
| 6,450,845 | B1 | 9/2002 | Snyder et al. |
| 6,454,708 | B1 | 9/2002 | Ferguson et al. |
| 6,456,256 | B1 | 9/2002 | Amundson et al. |
| 6,456,872 | B1 | 9/2002 | Faisandier |
| 6,463,320 | B1 | 10/2002 | Xue et al. |
| 6,469,669 | B1 | 10/2002 | Tran |
| 6,494,829 | B1 | 12/2002 | New, Jr. et al. |
| 6,505,069 | B2 | 1/2003 | Scott et al. |
| 6,546,285 | B1 | 4/2003 | Owen et al. |
| 6,605,046 | B1 | 8/2003 | Del Mar |
| 6,607,485 | B2 | 8/2003 | Bardy |
| 6,611,705 | B2 | 8/2003 | Hopman et al. |
| 6,623,312 | B2 | 9/2003 | Merry et al. |
| 6,671,545 | B2 | 12/2003 | Fincke |
| 6,671,547 | B2 | 12/2003 | Lyster et al. |
| 6,694,186 | B2 | 2/2004 | Bardy |
| 6,704,595 | B2 | 3/2004 | Bardy |
| 6,705,991 | B2 | 3/2004 | Bardy |
| 6,719,701 | B2 | 4/2004 | Lade |
| 6,754,523 | B2 | 6/2004 | Toole |
| 6,782,293 | B2 | 8/2004 | Dupelle et al. |
| 6,856,832 | B1 | 2/2005 | Matsumura |
| 6,860,897 | B2 | 3/2005 | Bardy |
| 6,866,629 | B2 | 3/2005 | Bardy |
| 6,887,201 | B2 | 5/2005 | Bardy |
| 6,893,397 | B2 | 5/2005 | Bardy |
| 6,895,261 | B1 | 5/2005 | Palamides |
| 6,904,312 | B2 | 6/2005 | Bardy |
| 6,908,431 | B2 | 6/2005 | Bardy |
| 6,913,577 | B2 | 7/2005 | Bardy |
| 6,944,498 | B2 | 9/2005 | Owen et al. |
| 6,960,167 | B2 | 11/2005 | Bardy |
| 6,970,731 | B1 | 11/2005 | Jayaraman et al. |
| 6,978,169 | B1 | 12/2005 | Guerra |
| 6,993,377 | B2 | 1/2006 | Flick et al. |
| 7,020,508 | B2 | 3/2006 | Stivoric et al. |
| 7,027,864 | B2 | 4/2006 | Snyder et al. |
| 7,052,472 | B1 | 5/2006 | Miller et al. |
| 7,065,401 | B2 | 6/2006 | Worden |
| 7,085,601 | B1 | 8/2006 | Bardy et al. |
| 7,104,955 | B2 | 9/2006 | Bardy |
| 7,134,996 | B2 | 11/2006 | Bardy |
| 7,137,389 | B2 | 11/2006 | Berthon-Jones |
| 7,147,600 | B2 | 12/2006 | Bardy |
| 7,153,265 | B2 | 12/2006 | Vachon |
| 7,187,985 | B2 | 3/2007 | Carim |
| 7,197,357 | B2 | 3/2007 | Istvan et al. |
| 7,206,630 | B1 | 4/2007 | Tarler |
| 7,212,849 | B2 | 5/2007 | Zhang et al. |
| 7,215,991 | B2 | 5/2007 | Besson et al. |
| 7,248,916 | B2 | 7/2007 | Bardy |
| 7,257,438 | B2 | 8/2007 | Kinast |
| 7,277,752 | B2 | 10/2007 | Matos |
| 7,294,108 | B1 | 11/2007 | Bornzin et al. |
| D558,882 | S | 1/2008 | Brady |
| 7,328,061 | B2 | 2/2008 | Rowlandson et al. |
| 7,382,247 | B2 | 6/2008 | Welch et al. |
| 7,395,106 | B2 | 7/2008 | Ryu et al. |
| 7,412,395 | B2 | 8/2008 | Rowlandson et al. |
| 7,429,938 | B1 | 9/2008 | Comdorf |
| 7,433,731 | B2 | 10/2008 | Matsumura et al. |
| 7,468,032 | B2 | 12/2008 | Stahmann et al. |
| 7,471,976 | B2 | 12/2008 | Lin et al. |
| 7,552,031 | B2 | 6/2009 | Vock et al. |
| 7,621,877 | B2 | 11/2009 | Schnall |
| D606,656 | S | 12/2009 | Kobayashi et al. |
| 7,664,552 | B2 | 2/2010 | Wahlstrand et al. |
| 7,672,714 | B2 | 3/2010 | Kuo et al. |
| 7,697,997 | B2 | 4/2010 | Hyatt et al. |
| 7,706,870 | B2 | 4/2010 | Shieh et al. |
| 7,756,721 | B1 | 7/2010 | Falchuk et al. |
| 7,761,143 | B2 | 7/2010 | Matsumura et al. |
| 7,787,943 | B2 | 8/2010 | McDonough |
| 7,874,993 | B2 | 1/2011 | Bardy |
| 7,881,785 | B2 | 2/2011 | Nassif et al. |
| 7,884,932 | B2 | 2/2011 | Wachernig |
| D639,437 | S | 6/2011 | Bishay et al. |
| 7,959,574 | B2 | 6/2011 | Bardy |
| 7,970,450 | B2 | 6/2011 | Kroecker et al. |
| 8,016,776 | B2 | 9/2011 | Bourget et al. |
| 8,108,035 | B1 | 1/2012 | Bharmi |
| 8,116,841 | B2 | 2/2012 | Bly et al. |
| 8,135,459 | B2 | 3/2012 | Bardy et al. |
| 8,150,502 | B2 | 4/2012 | Kumar et al. |
| 8,160,682 | B2 | 4/2012 | Kumar et al. |
| 8,172,761 | B1 | 5/2012 | Rulkov et al. |
| 8,180,425 | B2 | 5/2012 | Selvitelli et al. |
| 8,200,320 | B2 | 6/2012 | Kovacs |
| 8,214,007 | B2 | 7/2012 | Baker et al. |
| 8,231,539 | B2 | 7/2012 | Bardy |
| 8,231,540 | B2 | 7/2012 | Bardy |
| 8,239,012 | B2 | 8/2012 | Felix et al. |
| 8,244,335 | B2 | 8/2012 | Kumar et al. |
| 8,249,686 | B2 | 8/2012 | Libbus et al. |
| 8,260,414 | B2 | 9/2012 | Nassif et al. |
| 8,260,439 | B2 | 9/2012 | DiUbaldi et al. |
| 8,266,008 | B1 | 9/2012 | Siegal et al. |
| 8,277,378 | B2 | 10/2012 | Bardy |
| 8,285,356 | B2 | 10/2012 | Bly et al. |
| 8,285,370 | B2 | 10/2012 | Felix et al. |
| 8,308,650 | B2 | 11/2012 | Bardy |
| 8,315,695 | B2 | 11/2012 | Sebelius et al. |
| 8,334,464 | B2 | 12/2012 | Edwards et al. |
| 8,366,629 | B2 | 2/2013 | Bardy |
| 8,374,688 | B2 | 2/2013 | Libbus et al. |
| 8,412,317 | B2 | 4/2013 | Mazar |

(56)　　　　　References Cited

U.S. PATENT DOCUMENTS

| | | |
|---|---|---|
| 8,460,189 B2 | 6/2013 | Libbus et al. |
| 8,473,047 B2 | 6/2013 | Chakravarthy et al. |
| 8,478,418 B2 | 7/2013 | Fahey |
| 8,483,809 B2 | 7/2013 | Kim et al. |
| 8,538,503 B2 | 9/2013 | Kumar et al. |
| 8,545,416 B1 | 10/2013 | Kayyali et al. |
| 8,554,311 B2 | 10/2013 | Warner et al. |
| 8,560,046 B2 | 10/2013 | Kumar et al. |
| 8,591,430 B2 | 11/2013 | Amurthur et al. |
| 8,594,763 B1 | 11/2013 | Bibian et al. |
| 8,600,486 B2 | 12/2013 | Kaib et al. |
| 8,611,980 B2 | 12/2013 | Choe et al. |
| 8,613,708 B2 | 12/2013 | Bishay et al. |
| 8,613,709 B2 | 12/2013 | Bishay et al. |
| 8,615,282 B2 | 12/2013 | Brister et al. |
| 8,620,418 B1 | 12/2013 | Kuppuraj et al. |
| 8,626,262 B2 | 1/2014 | McGusty et al. |
| 8,626,277 B2 | 1/2014 | Felix et al. |
| 8,628,020 B2 | 1/2014 | Beck |
| 8,630,699 B2 | 1/2014 | Baker et al. |
| 8,632,463 B2 | 1/2014 | Drinan et al. |
| 8,647,268 B2 | 2/2014 | Tran |
| 8,668,653 B2 | 3/2014 | Nagata et al. |
| 8,684,925 B2 | 4/2014 | Manicka et al. |
| 8,688,190 B2 | 4/2014 | Libbus et al. |
| 8,718,736 B2 | 5/2014 | Gonopolskiy et al. |
| 8,718,742 B2 | 5/2014 | Beck et al. |
| 8,718,752 B2 | 5/2014 | Libbus et al. |
| 8,744,561 B2 | 6/2014 | Fahey |
| 8,750,974 B2 | 6/2014 | Baker et al. |
| 8,774,932 B2 | 7/2014 | Fahey |
| 8,790,257 B2 | 7/2014 | Libbus et al. |
| 8,790,259 B2 | 7/2014 | Katra et al. |
| 8,795,174 B2 | 8/2014 | Manicka et al. |
| 8,798,729 B2 | 8/2014 | Kaib et al. |
| 8,798,734 B2 | 8/2014 | Kuppuraj et al. |
| 8,818,478 B2 | 8/2014 | Scheffler et al. |
| 8,818,481 B2 | 8/2014 | Bly et al. |
| 8,823,490 B2 | 9/2014 | Libbus et al. |
| 8,858,432 B2 | 10/2014 | Robertson et al. |
| 8,911,383 B2 | 12/2014 | Christensen et al. |
| 8,926,509 B2 | 1/2015 | Magar et al. |
| 8,938,287 B2 | 1/2015 | Felix et al. |
| 8,948,935 B1 | 2/2015 | Peeters |
| 8,965,492 B2 | 2/2015 | Baker et al. |
| 8,983,594 B2 | 3/2015 | Saar et al. |
| 9,066,664 B2 | 6/2015 | Karjalainen |
| 9,135,608 B2 | 9/2015 | Herlitz |
| 9,149,229 B1 | 10/2015 | Tarler |
| 9,155,484 B2 | 10/2015 | Baker et al. |
| 9,173,670 B2 | 11/2015 | Sepulveda et al. |
| 9,183,738 B1 | 11/2015 | Allen, Sr. et al. |
| 9,204,813 B2 | 12/2015 | Kaib et al. |
| 9,211,073 B2 | 12/2015 | Banet et al. |
| 9,241,649 B2 | 1/2016 | Kumar et al. |
| 9,259,154 B2 | 2/2016 | Miller et al. |
| 9,267,793 B2 | 2/2016 | Vock et al. |
| 9,277,864 B2 | 3/2016 | Yang et al. |
| 9,277,871 B2 | 3/2016 | Keenan et al. |
| 9,339,202 B2 | 5/2016 | Brockway et al. |
| 9,375,179 B2 | 6/2016 | Schultz et al. |
| 9,414,786 B1 | 8/2016 | Brockway et al. |
| 9,433,366 B2 | 9/2016 | Baker et al. |
| 9,439,566 B2 | 9/2016 | Arne et al. |
| 9,451,975 B2 | 9/2016 | Sepulveda et al. |
| 9,469,599 B2 | 10/2016 | Kanj et al. |
| 9,510,755 B2 | 12/2016 | Fong et al. |
| 9,603,542 B2 | 3/2017 | Veen et al. |
| 9,669,212 B2 | 6/2017 | Mueller et al. |
| 9,693,732 B1 | 7/2017 | Tarler |
| 9,700,222 B2 | 7/2017 | Quinlan et al. |
| 9,757,554 B2 | 9/2017 | Dar et al. |
| 9,770,182 B2 | 9/2017 | Bly et al. |
| 9,877,663 B2 | 1/2018 | Baker et al. |
| 10,034,614 B2 | 7/2018 | Edic et al. |
| 10,045,708 B2 | 8/2018 | Dusan |
| 10,049,182 B2 | 8/2018 | Chefles et al. |
| 10,159,422 B2 | 12/2018 | Baker et al. |
| 10,244,949 B2 | 4/2019 | Moyer et al. |
| 10,271,754 B2 | 4/2019 | Bahney et al. |
| 10,327,660 B2 | 6/2019 | Gallego et al. |
| 10,405,799 B2 | 9/2019 | Kumar et al. |
| 10,413,251 B2 | 9/2019 | Golda et al. |
| 10,441,185 B2 | 10/2019 | Rogers et al. |
| 10,517,500 B2 | 12/2019 | Kumar et al. |
| 10,555,683 B2 | 2/2020 | Bahney et al. |
| 10,939,839 B2 | 3/2021 | Baker et al. |
| 11,051,738 B2 | 7/2021 | Bahney et al. |
| 11,051,743 B2 | 7/2021 | Felix et al. |
| 11,116,447 B2 | 9/2021 | Yang et al. |
| 11,141,091 B2 | 10/2021 | Kumar et al. |
| 11,445,967 B2 | 9/2022 | Felix et al. |
| 11,627,902 B2 | 4/2023 | Bahney et al. |
| 12,133,734 B2 | 11/2024 | Kumar et al. |
| 12,245,859 B2 | 3/2025 | Bahney et al. |
| 12,245,860 B2 | 3/2025 | Bahney et al. |
| 12,274,554 B2 | 4/2025 | Kumar et al. |
| 12,285,261 B2 | 4/2025 | Bishay et al. |
| 12,303,275 B2 | 5/2025 | Bahney et al. |
| 12,303,277 B2 | 5/2025 | Kumar et al. |
| 2001/0051766 A1 | 12/2001 | Gazdzinski |
| 2002/0013538 A1 | 1/2002 | Teller |
| 2002/0013717 A1 | 1/2002 | Ando et al. |
| 2002/0016798 A1 | 2/2002 | Sakai et al. |
| 2002/0072682 A1 | 6/2002 | Hopman |
| 2002/0082491 A1 | 6/2002 | Nissila |
| 2002/0082867 A1 | 6/2002 | MacCarter et al. |
| 2002/0099277 A1 | 7/2002 | Harry et al. |
| 2002/0103422 A1 | 8/2002 | Harder et al. |
| 2002/0106709 A1 | 8/2002 | Potts et al. |
| 2002/0107436 A1 | 8/2002 | Barton et al. |
| 2002/0109621 A1 | 8/2002 | Khair et al. |
| 2002/0120310 A1 | 8/2002 | Linden et al. |
| 2002/0128686 A1 | 9/2002 | Minogue et al. |
| 2002/0184055 A1 | 12/2002 | Naghavi et al. |
| 2002/0193668 A1 | 12/2002 | Munneke |
| 2003/0004547 A1 | 1/2003 | Owen et al. |
| 2003/0028811 A1 | 2/2003 | Walker et al. |
| 2003/0055460 A1 | 3/2003 | Owen et al. |
| 2003/0069510 A1 | 4/2003 | Semler et al. |
| 2003/0073916 A1 | 4/2003 | Yonce |
| 2003/0083559 A1 | 5/2003 | Thompson |
| 2003/0097078 A1 | 5/2003 | Maeda |
| 2003/0139785 A1 | 7/2003 | Riff et al. |
| 2003/0149349 A1 | 8/2003 | Jensen |
| 2003/0149439 A1 | 8/2003 | Wendlandt |
| 2003/0174881 A1 | 9/2003 | Simard et al. |
| 2003/0176802 A1 | 9/2003 | Galen et al. |
| 2003/0211797 A1 | 11/2003 | Hill et al. |
| 2003/0216662 A1 | 11/2003 | Jersey-Willuhn et al. |
| 2004/0008123 A1 | 1/2004 | Carrender |
| 2004/0019288 A1 | 1/2004 | Kinast |
| 2004/0034284 A1 | 2/2004 | Aversano et al. |
| 2004/0049120 A1 | 3/2004 | Cao et al. |
| 2004/0049132 A1 | 3/2004 | Barron et al. |
| 2004/0073127 A1 | 4/2004 | Stvan et al. |
| 2004/0087836 A1 | 5/2004 | Green et al. |
| 2004/0088019 A1 | 5/2004 | Rueter et al. |
| 2004/0093192 A1 | 5/2004 | Hasson et al. |
| 2004/0116784 A1 | 6/2004 | Gavish |
| 2004/0148194 A1 | 7/2004 | Wellons et al. |
| 2004/0163034 A1 | 8/2004 | Colbath et al. |
| 2004/0167416 A1 | 8/2004 | Lee |
| 2004/0171921 A1 | 9/2004 | Say et al. |
| 2004/0207530 A1 | 10/2004 | Nielsen |
| 2004/0210165 A1 | 10/2004 | Marmaropoulos et al. |
| 2004/0220486 A1 | 11/2004 | Baumer et al. |
| 2004/0236202 A1 | 11/2004 | Burton |
| 2004/0243435 A1 | 12/2004 | Williams |
| 2004/0256453 A1 | 12/2004 | Lammle |
| 2004/0260188 A1 | 12/2004 | Syed et al. |
| 2004/0260192 A1 | 12/2004 | Yamamoto |
| 2005/0010139 A1 | 1/2005 | Aminian et al. |
| 2005/0043640 A1 | 2/2005 | Chang |

(56) References Cited

U.S. PATENT DOCUMENTS

| | | |
|---|---|---|
| 2005/0058701 A1 | 3/2005 | Gross et al. |
| 2005/0096513 A1 | 5/2005 | Ozguz et al. |
| 2005/0096717 A1 | 5/2005 | Bishay et al. |
| 2005/0101875 A1 | 5/2005 | Semler et al. |
| 2005/0108055 A1 | 5/2005 | Ott et al. |
| 2005/0113661 A1 | 5/2005 | Nazeri |
| 2005/0137485 A1 | 6/2005 | Cao et al. |
| 2005/0151640 A1 | 7/2005 | Hastings |
| 2005/0154267 A1 | 7/2005 | Bardy |
| 2005/0154294 A1 | 7/2005 | Uchiyama et al. |
| 2005/0182308 A1 | 8/2005 | Bardy |
| 2005/0182309 A1 | 8/2005 | Bardy |
| 2005/0215918 A1 | 9/2005 | Frantz et al. |
| 2005/0222513 A1 | 10/2005 | Hadley et al. |
| 2005/0228243 A1 | 10/2005 | Bardy |
| 2005/0245797 A1 | 11/2005 | Al-Ali et al. |
| 2005/0245839 A1 | 11/2005 | Stivoric et al. |
| 2005/0261564 A1 | 11/2005 | Ryu et al. |
| 2005/0275416 A1 | 12/2005 | Hervieux et al. |
| 2006/0020217 A1 | 1/2006 | Lin |
| 2006/0025696 A1 | 2/2006 | Kurzweil et al. |
| 2006/0025824 A1 | 2/2006 | Freeman et al. |
| 2006/0030767 A1 | 2/2006 | Lang et al. |
| 2006/0030781 A1 | 2/2006 | Shennib |
| 2006/0030904 A1 | 2/2006 | Quiles |
| 2006/0041201 A1 | 2/2006 | Behbehani et al. |
| 2006/0052999 A1 | 3/2006 | Brooks et al. |
| 2006/0084883 A1 | 4/2006 | Linker |
| 2006/0100530 A1 | 5/2006 | Kliot et al. |
| 2006/0111642 A1 | 5/2006 | Baura et al. |
| 2006/0111943 A1 | 5/2006 | Wu |
| 2006/0122469 A1 | 6/2006 | Martel |
| 2006/0124193 A1 | 6/2006 | Orr et al. |
| 2006/0167502 A1 | 7/2006 | Haefner |
| 2006/0224072 A1 | 10/2006 | Shennib |
| 2006/0229522 A1 | 10/2006 | Barr |
| 2006/0235316 A1 | 10/2006 | Ungless et al. |
| 2006/0235320 A1 | 10/2006 | Tan et al. |
| 2006/0238333 A1 | 10/2006 | Welch et al. |
| 2006/0247509 A1 | 11/2006 | Tuccillo et al. |
| 2006/0253006 A1 | 11/2006 | Bardy |
| 2006/0264730 A1 | 11/2006 | Stivoric et al. |
| 2006/0264767 A1 | 11/2006 | Shennib |
| 2006/0282001 A1 | 12/2006 | Noel et al. |
| 2007/0003115 A1 | 1/2007 | Patton et al. |
| 2007/0029961 A1 | 2/2007 | Harita et al. |
| 2007/0038057 A1 | 2/2007 | Nam et al. |
| 2007/0050209 A1 | 3/2007 | Yered |
| 2007/0060862 A1 | 3/2007 | Sun et al. |
| 2007/0069887 A1 | 3/2007 | Welch et al. |
| 2007/0073132 A1 | 3/2007 | Vosch |
| 2007/0078324 A1 | 4/2007 | Wijisiriwardana |
| 2007/0078354 A1 | 4/2007 | Holland |
| 2007/0088406 A1 | 4/2007 | Bennett et al. |
| 2007/0088419 A1 | 4/2007 | Fiorina et al. |
| 2007/0088429 A1 | 4/2007 | Thompson |
| 2007/0089800 A1 | 4/2007 | Sharma |
| 2007/0093719 A1 | 4/2007 | Nichols, Jr. et al. |
| 2007/0100248 A1 | 5/2007 | Van Dam et al. |
| 2007/0100666 A1 | 5/2007 | Stivoric et al. |
| 2007/0100667 A1 | 5/2007 | Bardy |
| 2007/0123801 A1 | 5/2007 | Goldberger et al. |
| 2007/0131595 A1 | 6/2007 | Jansson et al. |
| 2007/0136091 A1 | 6/2007 | McTaggart |
| 2007/0142722 A1 | 6/2007 | Chang |
| 2007/0173892 A1 | 7/2007 | Fleischer et al. |
| 2007/0179357 A1 | 8/2007 | Bardy |
| 2007/0185390 A1 | 8/2007 | Perkins et al. |
| 2007/0203415 A1 | 8/2007 | Bardy |
| 2007/0203423 A1 | 8/2007 | Bardy |
| 2007/0206655 A1 | 9/2007 | Haslett et al. |
| 2007/0208232 A1 | 9/2007 | Kovacs |
| 2007/0208233 A1 | 9/2007 | Kovacs |
| 2007/0208266 A1 | 9/2007 | Hadley |
| 2007/0225611 A1 | 9/2007 | Kumar et al. |
| 2007/0233198 A1 | 10/2007 | Ghanem et al. |
| 2007/0244405 A1 | 10/2007 | Xue et al. |
| 2007/0249946 A1 | 10/2007 | Kumar et al. |
| 2007/0255153 A1 | 11/2007 | Kumar et al. |
| 2007/0265510 A1 | 11/2007 | Bardy |
| 2007/0270678 A1 | 11/2007 | Fadem et al. |
| 2007/0276270 A1 | 11/2007 | Tran |
| 2007/0276275 A1 | 11/2007 | Proctor et al. |
| 2007/0293738 A1 | 12/2007 | Bardy |
| 2007/0293739 A1 | 12/2007 | Bardy |
| 2007/0293740 A1 | 12/2007 | Bardy |
| 2007/0293741 A1 | 12/2007 | Bardy |
| 2007/0293772 A1 | 12/2007 | Bardy |
| 2007/0293781 A1 | 12/2007 | Sims et al. |
| 2007/0299325 A1 | 12/2007 | Farrell et al. |
| 2007/0299617 A1 | 12/2007 | Willis |
| 2008/0027337 A1 | 1/2008 | Dugan |
| 2008/0027339 A1 | 1/2008 | Nagai et al. |
| 2008/0051668 A1 | 2/2008 | Bardy |
| 2008/0058661 A1 | 3/2008 | Bardy |
| 2008/0088467 A1 | 4/2008 | Al-Ali et al. |
| 2008/0091089 A1 | 4/2008 | Guillory et al. |
| 2008/0091090 A1 | 4/2008 | Guillory et al. |
| 2008/0091097 A1 | 4/2008 | Linti et al. |
| 2008/0108889 A1 | 5/2008 | Lin et al. |
| 2008/0108890 A1 | 5/2008 | Teng et al. |
| 2008/0114232 A1 | 5/2008 | Gazit |
| 2008/0139953 A1 | 6/2008 | Baker et al. |
| 2008/0143080 A1 | 6/2008 | Burr |
| 2008/0171918 A1 | 7/2008 | Teller et al. |
| 2008/0177168 A1 | 7/2008 | Callahan et al. |
| 2008/0182204 A1 | 7/2008 | Calvert et al. |
| 2008/0194927 A1 | 8/2008 | KenKnight et al. |
| 2008/0208009 A1 | 8/2008 | Shklarski |
| 2008/0208014 A1 | 8/2008 | KenKnight et al. |
| 2008/0214949 A1 | 9/2008 | Stivoric et al. |
| 2008/0214985 A1 | 9/2008 | Yanaki |
| 2008/0243012 A1 | 10/2008 | Fujihashi et al. |
| 2008/0269657 A1 | 10/2008 | Brenneman et al. |
| 2008/0284599 A1 | 11/2008 | Zdeblick et al. |
| 2008/0288026 A1 | 11/2008 | Cross et al. |
| 2008/0294024 A1 | 11/2008 | Cosentino et al. |
| 2008/0306359 A1 | 12/2008 | Zdeblick et al. |
| 2008/0306397 A1 | 12/2008 | Bonmassar et al. |
| 2008/0309481 A1 | 12/2008 | Tanaka et al. |
| 2008/0312522 A1 | 12/2008 | Rowlandson et al. |
| 2008/0312524 A1 | 12/2008 | Solosko et al. |
| 2009/0009342 A1 | 1/2009 | Karjalainen |
| 2009/0012412 A1 | 1/2009 | Wiesel |
| 2009/0012979 A1 | 1/2009 | Bateni et al. |
| 2009/0048563 A1 | 2/2009 | Ethelfeld et al. |
| 2009/0054737 A1 | 2/2009 | Magar et al. |
| 2009/0054952 A1 | 2/2009 | Glukhovsky et al. |
| 2009/0062670 A1 | 3/2009 | Sterling et al. |
| 2009/0062897 A1 | 3/2009 | Axelgaard |
| 2009/0069867 A1 | 3/2009 | KenKnight et al. |
| 2009/0073991 A1 | 3/2009 | Landrum et al. |
| 2009/0076336 A1 | 3/2009 | Mazar et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076345 A1 | 3/2009 | Manicka et al. |
| 2009/0076346 A1 | 3/2009 | James et al. |
| 2009/0076349 A1 | 3/2009 | Libbus et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076401 A1 | 3/2009 | Mazar et al. |
| 2009/0076559 A1 | 3/2009 | Libbus et al. |
| 2009/0088652 A1 | 4/2009 | Tremblay |
| 2009/0093687 A1 | 4/2009 | Telfort et al. |
| 2009/0099469 A1 | 4/2009 | Flores |
| 2009/0105632 A1 | 4/2009 | Padmanabhan et al. |
| 2009/0112116 A1 | 4/2009 | Lee et al. |
| 2009/0131759 A1 | 5/2009 | Sims et al. |
| 2009/0133047 A1 | 5/2009 | Lee et al. |
| 2009/0156908 A1 | 6/2009 | Belalcazar et al. |
| 2009/0171258 A1 | 7/2009 | Stroebeck et al. |
| 2009/0177068 A1 | 7/2009 | Stivoric et al. |

(56) References Cited

U.S. PATENT DOCUMENTS

| | | |
|---|---|---|
| 2009/0177073 A1 | 7/2009 | Sonnenborg |
| 2009/0182204 A1 | 7/2009 | Semler et al. |
| 2009/0216132 A1 | 8/2009 | Orbach |
| 2009/0264792 A1 | 10/2009 | Mazar |
| 2009/0270708 A1 | 10/2009 | Shen et al. |
| 2009/0270747 A1 | 10/2009 | Van Dam et al. |
| 2009/0292194 A1 | 11/2009 | Libbus et al. |
| 2009/0327715 A1 | 12/2009 | Smith et al. |
| 2010/0007413 A1 | 1/2010 | Herleikson et al. |
| 2010/0016701 A1 | 1/2010 | Cheng et al. |
| 2010/0022897 A1 | 1/2010 | Parker et al. |
| 2010/0056877 A1 | 3/2010 | Fein et al. |
| 2010/0056881 A1 | 3/2010 | Libbus et al. |
| 2010/0056972 A1 | 3/2010 | Harima et al. |
| 2010/0063365 A1 | 3/2010 | Pisani et al. |
| 2010/0076517 A1 | 3/2010 | Imran |
| 2010/0081913 A1 | 4/2010 | Cross et al. |
| 2010/0137694 A1 | 6/2010 | Irazoqui et al. |
| 2010/0174229 A1 | 7/2010 | Hsu et al. |
| 2010/0177100 A1 | 7/2010 | Carnes et al. |
| 2010/0185063 A1 | 7/2010 | Bardy |
| 2010/0185076 A1 | 7/2010 | Jeong et al. |
| 2010/0191154 A1 | 7/2010 | Berger et al. |
| 2010/0191310 A1 | 7/2010 | Bly |
| 2010/0223020 A1 | 9/2010 | Goetz |
| 2010/0234697 A1 | 9/2010 | Walter et al. |
| 2010/0234700 A1 | 9/2010 | Bowers |
| 2010/0234715 A1 | 9/2010 | Shin et al. |
| 2010/0234716 A1 | 9/2010 | Engel |
| 2010/0268103 A1 | 10/2010 | McNamara et al. |
| 2010/0280366 A1 | 11/2010 | Arne et al. |
| 2010/0298720 A1 | 11/2010 | Potkay |
| 2010/0305416 A1 | 12/2010 | Bédard et al. |
| 2010/0312188 A1 | 12/2010 | Robertson et al. |
| 2010/0317957 A1 | 12/2010 | Lee et al. |
| 2010/0324384 A1 | 12/2010 | Moon et al. |
| 2010/0324405 A1 | 12/2010 | Niemi et al. |
| 2011/0006902 A1 | 1/2011 | Saigh |
| 2011/0009729 A1 | 1/2011 | Shin et al. |
| 2011/0021937 A1 | 1/2011 | Hugh et al. |
| 2011/0054285 A1 | 3/2011 | Searle et al. |
| 2011/0054286 A1 | 3/2011 | Crosby et al. |
| 2011/0060215 A1 | 3/2011 | Tupin et al. |
| 2011/0066041 A1 | 3/2011 | Pandia et al. |
| 2011/0077497 A1 | 3/2011 | Oster et al. |
| 2011/0082842 A1 | 4/2011 | Groseclose, Jr. et al. |
| 2011/0098549 A1 | 4/2011 | Bar Hayim et al. |
| 2011/0105861 A1 | 5/2011 | Derchak et al. |
| 2011/0112379 A1 | 5/2011 | Li et al. |
| 2011/0125040 A1 | 5/2011 | Crawford et al. |
| 2011/0144470 A1 | 6/2011 | Mazar et al. |
| 2011/0160548 A1 | 6/2011 | Forster |
| 2011/0160601 A1 | 6/2011 | Wang et al. |
| 2011/0166529 A1 | 7/2011 | LeLievre et al. |
| 2011/0208076 A1 | 8/2011 | Fong et al. |
| 2011/0224564 A1 | 9/2011 | Moon et al. |
| 2011/0230739 A1 | 9/2011 | Gretz et al. |
| 2011/0237922 A1 | 9/2011 | Parker, III et al. |
| 2011/0237924 A1 | 9/2011 | McGusty et al. |
| 2011/0245648 A1 | 10/2011 | Hudson |
| 2011/0245699 A1 | 10/2011 | Snell et al. |
| 2011/0245711 A1 | 10/2011 | Katra et al. |
| 2011/0279963 A1 | 11/2011 | Kumar et al. |
| 2011/0288605 A1 | 11/2011 | Kaib et al. |
| 2011/0301490 A1 | 12/2011 | Mucke et al. |
| 2011/0313305 A1 | 12/2011 | Rantala |
| 2012/0003933 A1 | 1/2012 | Baker et al. |
| 2012/0029300 A1 | 2/2012 | Paquet |
| 2012/0029306 A1 | 2/2012 | Paquet et al. |
| 2012/0029307 A1 | 2/2012 | Paquet et al. |
| 2012/0029309 A1 | 2/2012 | Paquet et al. |
| 2012/0029314 A1 | 2/2012 | Paquet et al. |
| 2012/0029315 A1 | 2/2012 | Raptis et al. |
| 2012/0029316 A1 | 2/2012 | Raptis et al. |
| 2012/0035432 A1 | 2/2012 | Katra et al. |
| 2012/0059668 A1 | 3/2012 | Baldock et al. |
| 2012/0078127 A1 | 3/2012 | McDonald et al. |
| 2012/0079127 A1 | 3/2012 | Hadland |
| 2012/0088998 A1 | 4/2012 | Bardy et al. |
| 2012/0088999 A1 | 4/2012 | Bishay et al. |
| 2012/0089000 A1 | 4/2012 | Bishay et al. |
| 2012/0089001 A1 | 4/2012 | Bishay et al. |
| 2012/0089037 A1 | 4/2012 | Bishay et al. |
| 2012/0089412 A1 | 4/2012 | Bardy et al. |
| 2012/0089417 A1 | 4/2012 | Bardy et al. |
| 2012/0095352 A1 | 4/2012 | Tran |
| 2012/0101358 A1 | 4/2012 | Boettcher et al. |
| 2012/0101396 A1 | 4/2012 | Solosko et al. |
| 2012/0108917 A1 | 5/2012 | Libbus et al. |
| 2012/0108993 A1 | 5/2012 | Gordon et al. |
| 2012/0158075 A1 | 6/2012 | Kaib et al. |
| 2012/0165645 A1 | 6/2012 | Russel et al. |
| 2012/0172695 A1 | 7/2012 | Ko et al. |
| 2012/0179665 A1 | 7/2012 | Baarman et al. |
| 2012/0184207 A1 | 7/2012 | Gaines |
| 2012/0197118 A1 | 8/2012 | Lisiecki et al. |
| 2012/0215123 A1 | 8/2012 | Kumar et al. |
| 2012/0220835 A1 | 8/2012 | Chung |
| 2012/0232929 A1 | 9/2012 | Experton |
| 2012/0238910 A1 | 9/2012 | Nordstrom |
| 2012/0253847 A1 | 10/2012 | Dell'Anno et al. |
| 2012/0265080 A1 | 10/2012 | Yu et al. |
| 2012/0265738 A1 | 10/2012 | Beckmann et al. |
| 2012/0302906 A1 | 11/2012 | Felix et al. |
| 2012/0306662 A1 | 12/2012 | Vosch et al. |
| 2012/0323098 A1 | 12/2012 | Moein et al. |
| 2012/0323132 A1 | 12/2012 | Warner et al. |
| 2012/0330126 A1 | 12/2012 | Hoppe et al. |
| 2013/0041272 A1 | 2/2013 | Javier et al. |
| 2013/0077263 A1 | 3/2013 | Oleson et al. |
| 2013/0079611 A1 | 3/2013 | Besko |
| 2013/0079618 A1 | 3/2013 | Sandmore et al. |
| 2013/0085347 A1 | 4/2013 | Manicka et al. |
| 2013/0085403 A1 | 4/2013 | Gunderson et al. |
| 2013/0087609 A1 | 4/2013 | Nichol et al. |
| 2013/0096395 A1 | 4/2013 | Katra et al. |
| 2013/0109937 A1 | 5/2013 | Banet et al. |
| 2013/0116533 A1 | 5/2013 | Lian et al. |
| 2013/0123651 A1 | 5/2013 | Bardy |
| 2013/0124891 A1 | 5/2013 | Donaldson |
| 2013/0131530 A1 | 5/2013 | Brockway et al. |
| 2013/0158361 A1 | 6/2013 | Bardy |
| 2013/0172763 A1 | 7/2013 | Wheeler |
| 2013/0197341 A1 | 8/2013 | Grob et al. |
| 2013/0197380 A1 | 8/2013 | Oral et al. |
| 2013/0225963 A1 | 8/2013 | Kodandaramaiah et al. |
| 2013/0225966 A1 | 8/2013 | Barber et al. |
| 2013/0225967 A1 | 8/2013 | Esposito |
| 2013/0226018 A1 | 8/2013 | Kumar et al. |
| 2013/0231947 A1 | 9/2013 | Shusterman |
| 2013/0243105 A1 | 9/2013 | Lei et al. |
| 2013/0274565 A1 | 10/2013 | Langer et al. |
| 2013/0274584 A1 | 10/2013 | Finlay et al. |
| 2013/0275158 A1 | 10/2013 | Fahey |
| 2013/0324809 A1 | 12/2013 | Lisogurski et al. |
| 2013/0324855 A1 | 12/2013 | Lisogurski et al. |
| 2013/0324856 A1 | 12/2013 | Lisogurski et al. |
| 2013/0325081 A1 | 12/2013 | Karst et al. |
| 2013/0325096 A1 | 12/2013 | Dupelle et al. |
| 2013/0325359 A1 | 12/2013 | Jarverud et al. |
| 2013/0331665 A1 | 12/2013 | Libbus et al. |
| 2013/0338448 A1 | 12/2013 | Libbus et al. |
| 2013/0338472 A1 | 12/2013 | Barber et al. |
| 2014/0002234 A1 | 1/2014 | Alwan |
| 2014/0005502 A1 | 1/2014 | Klap et al. |
| 2014/0012154 A1 | 1/2014 | Mazar et al. |
| 2014/0031663 A1 | 1/2014 | Gallego |
| 2014/0056452 A1 | 2/2014 | Moss et al. |
| 2014/0088399 A1 | 3/2014 | Lian et al. |
| 2014/0094676 A1 | 4/2014 | Gani et al. |
| 2014/0107509 A1 | 4/2014 | Banet et al. |
| 2014/0121557 A1 | 5/2014 | Gannon et al. |
| 2014/0140359 A1 | 5/2014 | Kalevo et al. |
| 2014/0142411 A1 | 5/2014 | Lin et al. |

(56) References Cited

U.S. PATENT DOCUMENTS

| | | |
|---|---|---|
| 2014/0148718 A1 | 5/2014 | Stickney et al. |
| 2014/0180027 A1 | 6/2014 | Buller |
| 2014/0189928 A1 | 7/2014 | Oleson et al. |
| 2014/0194760 A1 | 7/2014 | Albert |
| 2014/0206977 A1 | 7/2014 | Bahney et al. |
| 2014/0213937 A1 | 7/2014 | Bianchi et al. |
| 2014/0214134 A1 | 7/2014 | Peterson |
| 2014/0215246 A1 | 7/2014 | Lee et al. |
| 2014/0228656 A1 | 8/2014 | Gonopolskiy et al. |
| 2014/0249852 A1 | 9/2014 | Proud |
| 2014/0280027 A1 | 9/2014 | Cordes et al. |
| 2014/0296651 A1 | 10/2014 | Stone |
| 2014/0297310 A1 | 10/2014 | Collins |
| 2014/0318699 A1 | 10/2014 | Longinotti-Buitoni et al. |
| 2014/0330147 A1 | 11/2014 | Ousdigian et al. |
| 2014/0343390 A1 | 11/2014 | Berzowska et al. |
| 2014/0358193 A1 | 12/2014 | Lyons et al. |
| 2014/0364756 A1 | 12/2014 | Brockway et al. |
| 2015/0018660 A1 | 1/2015 | Thomson et al. |
| 2015/0022372 A1 | 1/2015 | Vosch |
| 2015/0048836 A1 | 2/2015 | Guthrie et al. |
| 2015/0065842 A1 | 3/2015 | Lee et al. |
| 2015/0087950 A1 | 3/2015 | Felix et al. |
| 2015/0094558 A1 | 4/2015 | Russell |
| 2015/0142090 A1 | 5/2015 | Duijsens et al. |
| 2015/0177175 A1 | 6/2015 | Elder et al. |
| 2015/0202351 A1 | 7/2015 | Kaplan et al. |
| 2015/0250422 A1 | 9/2015 | Bay |
| 2015/0257670 A1 | 9/2015 | Ortega et al. |
| 2015/0305676 A1 | 10/2015 | Shoshani |
| 2015/0335285 A1 | 11/2015 | Poon et al. |
| 2015/0342526 A1 | 12/2015 | Totman et al. |
| 2015/0359489 A1 | 12/2015 | Baudenbacher et al. |
| 2016/0029917 A1 | 2/2016 | Baker et al. |
| 2016/0135746 A1 | 5/2016 | Kumar et al. |
| 2016/0217691 A1 | 7/2016 | Kadobayashi et al. |
| 2018/0020931 A1 | 1/2018 | Shusterman |
| 2019/0021671 A1 | 1/2019 | Kumar et al. |
| 2019/0117068 A1 | 4/2019 | Thomson et al. |
| 2019/0223806 A1 | 7/2019 | Bennet et al. |
| 2020/0121209 A1 | 4/2020 | Kumar et al. |
| 2021/0315504 A1 | 10/2021 | Kumar et al. |
| 2023/0248288 A1 | 8/2023 | Bahney et al. |
| 2024/0398310 A1 | 12/2024 | Kumar et al. |

FOREIGN PATENT DOCUMENTS

| | | |
|---|---|---|
| CN | 101163440 A | 4/2008 |
| DE | 19611414 A1 | 9/1997 |
| DE | 29805334 U1 | 7/1998 |
| DE | 19955211 | 5/2001 |
| DE | 10347303 A1 | 5/2005 |
| DE | 102004007712 A1 | 10/2005 |
| EP | 1090583 A1 | 4/2001 |
| EP | 1782730 A1 | 5/2007 |
| EP | 1859833 | 11/2007 |
| EP | 2081488 A2 | 7/2009 |
| EP | 1979040 B1 | 9/2009 |
| EP | 2438851 | 4/2012 |
| EP | 2438852 | 4/2012 |
| EP | 2465415 | 6/2012 |
| EP | 2589333 | 5/2013 |
| GB | 2350193 B | 4/2003 |
| JP | H06319711 | 11/1994 |
| JP | H11188015 | 7/1999 |
| JP | H11212159 A | 8/1999 |
| JP | 2002181641 A | 6/2002 |
| JP | 2004121360 | 4/2004 |
| JP | 2004129788 | 4/2004 |
| JP | 2005340087 A | 12/2005 |
| JP | 2007082938 | 4/2007 |
| JP | 2009219554 | 10/2009 |
| JP | 2012033508 A | 2/2012 |
| JP | 2012220849 A | 11/2012 |
| KR | 20120087633 A | 8/2012 |
| KR | 20120112879 A | 10/2012 |
| WO | 8701024 | 2/1987 |
| WO | 9632058 A1 | 10/1996 |
| WO | 9843537 A1 | 10/1998 |
| WO | 199852463 | 11/1998 |
| WO | 9913765 A1 | 3/1999 |
| WO | 9959465 A1 | 11/1999 |
| WO | 0078213 | 12/2000 |
| WO | 2002022006 | 3/2002 |
| WO | 0332192 | 4/2003 |
| WO | 2003032192 | 4/2003 |
| WO | WO 03/065926 A2 | 8/2003 |
| WO | 2005084533 | 9/2005 |
| WO | 2006009767 | 1/2006 |
| WO | 2006014806 | 2/2006 |
| WO | 2006109072 | 10/2006 |
| WO | 2007066270 | 6/2007 |
| WO | 2007081745 A2 | 7/2007 |
| WO | 2007092543 | 8/2007 |
| WO | 2008005016 | 1/2008 |
| WO | 2008006150 A1 | 1/2008 |
| WO | 2008010216 | 1/2008 |
| WO | WO 2008/005015 A1 | 1/2008 |
| WO | 2008057884 | 5/2008 |
| WO | 2008092098 | 7/2008 |
| WO | 2009036306 | 3/2009 |
| WO | 2009036313 | 3/2009 |
| WO | 2009036327 | 3/2009 |
| WO | 2009050702 A2 | 4/2009 |
| WO | 2009083980 A2 | 7/2009 |
| WO | 2009112976 | 9/2009 |
| WO | 2009112978 | 9/2009 |
| WO | 2009112979 | 9/2009 |
| WO | 2009142975 | 11/2009 |
| WO | 2010066507 | 6/2010 |
| WO | 2010104952 | 9/2010 |
| WO | 2010104952 A2 | 9/2010 |
| WO | 2010105045 | 9/2010 |
| WO | 2010107913 A2 | 9/2010 |
| WO | 2011047207 | 4/2011 |
| WO | 2012040487 | 3/2012 |
| WO | 2012104657 | 8/2012 |
| WO | 2012112407 | 8/2012 |
| WO | 2012125424 A2 | 9/2012 |
| WO | 2012125425 A2 | 9/2012 |
| WO | 2012140559 | 10/2012 |
| WO | 2012146957 | 11/2012 |
| WO | 2012149466 A2 | 11/2012 |

OTHER PUBLICATIONS 15 of the Hottest Wearable Gadgets, URL <http://thehottestgadgets.com/2008/09/the-15-hottest-wearable-gadgets-001253> (Web page cached on Sep. 27, 2008).

Alivecor, URL <http://www.businesswire.com/news/home/20121203005545/en/AliveCor%E2%80%99s-Heart-Monitor-Phone-Receives-FDA-Clearance#.U7rtq7FVTyF> (Dec. 3, 2012).

Bharadwaj et al., Techniques for Accurate ECG signal processing, EE Times, URL <www.eetimes.com/document.asp?doc_id=1278571> (Feb. 14, 2011).

Chen et al. "Monitoring Body Temperature of Newborn Infants at Neonatal Intensive Care Units Using Wearable Sensors," BodyNets 2010, Corfu Island, Greece. Sep. 10-12, 1210.

Epstein, Andrew E. et al.; ACC/AHA/HRS 2008 Guidelines for Device-Based Therapy of Cardiac Rhythm Abnormalities. J. Am. Coll. Cardiol. 2008; 51; el-e62, 66 Pgs.

Fitbit Tracker, URL <http://www.fitbit.com/> (Web page cached on Sep. 10, 2008.).

Smith, Jawbone Up, URL <http://www.businessinsider.com/fitbit-flex-vs-jawbone-up-2013-5?op=1> (Jun. 1, 2013).

Kligfield, Paul et al., Recommendations for the Standardization and Interpretation of the Electrocardiogram: Part I. J.Am.Coll. Cardiol; 2007; 49; 1109-27, 75 Pgs.

Lauren Gravitz, "When Your Diet Needs a Band-Aid," Technology Review, MIT. (May 1, 2009).

(56)         References Cited

OTHER PUBLICATIONS

Lieberman, Jonathan, "How Telemedicine Is Aiding Prompt ECG Diagnosis in Primary Care," British Journal of Community Nursing, vol. 13, No. 3, Mar. 1, 2008 (Mar. 1, 2008), pp. 123-126, XP009155082, ISSN: 1462-4753.

McManus et al., "A Novel Application for the Detection of an Irregular Pulse using an iPhone 4S in Patients with Atrial Fibrillation," vol. 10(3), pp. 315-319 (Mar. 2013.).

Nike+ Fuel Band, URL <http://www.nike.com/us/en_us/c/nikeplus-fuelband> (Web page cached on Jan. 11, 2013.).

P. Libby et al.,"Braunwald's Heart Disease—A Textbook of Cardiovascular Medicine," Chs. 11, pp. 125-148 and 12, pp. 149-193 (8th ed. 2008), American Heart Association.

Initial hands-on with Polar Loop activity tracker, URL <http://www.dcrainmaker.com/2013/09/polar-loop-firstlook.html> (Sep. 17, 2013).

Sittig et al., "A Computer-Based Outpatient Clinical Referral System," International Journal of Medical Informatics, Shannon, IR, vol. 55, No. 2, Aug. 1, 1999, pp. 149-158, XO004262434, ISSN: 1386-5056(99)00027-1.

Sleepview, URL <http://www.clevemed.com/sleepview/overview.shtml> (Web page cached on Sep. 4, 2013.).

Actigraphy/ Circadian Rhythm SOMNOwatch, URL <http://www.somnomedics.eu/news-events/publications/somnowatchtm.html> (Web page cached on Jan. 23, 2010).

Zio Event Card, URL <http://www.irhythmtech.com/zio-solution/zio-event/> (Web page cached on Mar. 11, 2013.).

Zio Patch System, URL <http://www.irhythmtech.com/zio-solution/zio-system/index.html> (Web page cached on Sep. 8, 2013.).

Saadi et al. "Heart Rhythm Analysis Using ECG Recorded With a Novel Sternum Based Patch Technology—A Pilot Study." Cardiotechnix 2013—Proceedings of the International Congress on Cardiovascular Technologies, Sep. 20, 2013.

Anonymous. "Omegawave Launches Consumer App 2.0 in U.S. Endurance Sportswire—Endurance Sportswire." Jul. 11, 2013. URL:http://endurancesportswire.com/omegawave-launches-consumer-app-2-0-in-u-s/.

Chan et al. "Wireless Patch Sensor for Remote Monitoring of Heart Rate, Respiration, Activity, and Falls." pp. 6115-6118. 2013 35th Annual International Conference of the IEEE Engineering in Medical and Biology Society.

Daoud et al. "Fall Detection Using Shimmer Technology and Multiresolution Analysis." Aug. 2, 2013. URL: https://decibel.ni.com/content/docs/DOC-26652.

Libbus. "Adherent Cardiac Monitor With Wireless Fall Detection for Patients With Unexplained Syncope." Abstracts of the First AMA-IEEE Medical Technology Conference on Individualized Healthcare. May 22, 2010.

Duttweiler et al., "Probability Estimation In Arithmetic and Adaptive-Huffman Entropy Coders," IEEE Transactions on Image Processing. vol. 4, No. 3, Mar. 1, 1995, pp. 237-246.

Gupta et al., "An ECG Compression Technique For Telecardiology Application," India Conference (INDICON), 2011 Annual IEEE, Dec. 16, 2011, pp. 1-4.

Nave et al., "ECG Compression Using Long-Term Prediction," IEEE Transactions on Biomedical Engineering, IEEE Service Center, NY, USA, vol. 40, No. 9, Sep. 1, 1993, pp. 877-885.

Skretting et al., "Improved Huffman Coding Using Recursive Splitting," NORSIG, Jan. 1, 1999.

A Voss et al., "Linear and Nonlinear Methods for Analyses of Cardiovascular Variability in Bipolar Disorders," Bipolar Disorders, votl. 8, No. 5p1, Oct. 1, 2006, pp. 441-452, XP55273826, DK ISSN: 1398-5647, DOI: 10.1111/i.1399-5618.2006.00364.x.

Varicrad-Kardi Software User's Manual Rev. 1.1, Jul. 8, 2009 (Jul. 8, 2009), XP002757888, retrieved from the Internet: URL:http://www.ehrlich.tv/KARDiVAR-Software.pdf [retrieved on May 20, 2016].

https://web.archive.org/web/20130831204020/http://www.biopac.com/research.asp?CatID=37&Main=Software (Aug. 2013).

Adinstruments:ECG Analysis Module for LabChart & PowerLab, 2008.

Biopac Systems, Inc. #AS148-Automated ECG Analysis , Mar. 24, 2006.

[Corrected] Chart CC-2 Invalidity Contentions: U.S. Pat. No. 11,445,967; Case No. 22-351-CJB (Delaware); Invalidity of U.S. Patent No. by U.S. Pat. Pub. No. 2011/0077497 ("Oster") and U.S. Pa. No. 11,116,447 ("Yang"); Oct. 25, 2023; 16 pages.

[Corrected] Chart C-2 Invalidity Contentions: U.S. Pat. No. 11,051,743; Case No. 22-351-CJB (Delaware); Invalidity of U.S. Pat. No. 11,051,743 by U.S. Pat. Pub. No. 2011/0077497 ("Oster") and U.S. Pat. No. 11,116,447 ("Yang"); Oct. 25, 2023; 22 pages.

Chart AA-1 Invalidity Contentions: U.S. Pat. No. 11,445,967; Case No. 22-351-CJB (Delaware); Invalidity of U.S. Pat. No. 11,445,967 by International Publication No. WO 2010/104952 to Mazar ("Mazar") and U.S. Pat. No. 11,116,447 ("Yang"); Oct. 25, 2023; 24 pages.

Chart C-1 Invalidity Contentions: U.S. Pat. No. 11,051,743; Case No. 22-351-CJB (Delaware); Invalidity of U.S. Pat. No. 11,051,743 by International Publication No. WO 2010/104952 to Mazar ("Mazar") and U.S. Pat. No. 11,116,447 ("Yang"); Oct. 25, 2023; 32 pages.

Chart B-7 Invalidity Contentions: U.S. Pat. No. 11,051,743 and U.S. Pat. No. 11,445,967; Case No. 22-351-CJB (Delaware); A Patch Comprising Adhered Layers; Oct. 25, 2023; 16 pages.

Chart B-6 Invalidity Contentions: U.S. Pat. No. 11,051,743 and U.S. Pat. No. 11,445,967; Case No. 22-351-CJB (Delaware); Hydrocolloid Adhesives on a Portion of the Backing; Oct. 25, 2023; 5 pages.

Chart B-5 Invalidity Contentions: U.S. Pat. No. 11,051,743 and U.S. Pat. No. 11,445,967; Case No. 22-351-CJB (Delaware); Conversion of Electrocardiogramals From One Format to Another; Oct. 25, 2023; 6 pages.

Chart B-4 Invalidity Contentions: U.S. Pat. No. 11,051,743 and U.S. Pat. No. 11,445,967; The Case No. 22-351-CJB (Delaware); Rounded Outer Edge of Backing Ends; Oct. 25, 2023; 5 pages.

Chart B-3 Invalidity Contentions: U.S. Pat. No. 11,051,743 and U.S. Pat. No. 11,445,967; Case No. 22-351-CJB (Delaware); Flexible Circuit Comprising a Pair of Circuit Traces to Couple Electrodes; Oct. 25, 2023; 8 pages.

Chart B-2 Invalidity Contentions: U.S. Pat. No. 11,051,743 and U.S. Pat. No. 11,445,967; Case No. 22-351-CJB (Delaware); An Electrocardiogramactrode on Each End of the Backing; Oct. 25, 2023; 8 pages.

Chart B-1 Invalidity Contentions: U.S. Pat. No. 11,051,743 and U.S. Pat. No. 11,445,967; Case No. 22-351-CJB (Delaware); Elongated Strip With Narrowed Midsection; Oct. 25, 2023; 8 pages.

Chart AA-10 Invalidity Contentions: U.S. Pat. No. 11,445,967; Case No. 22-351-CJB (Delaware); Invalidity of U.S. Pat. No. 11,445,967 by WO 2003/065926 ("Ozguz"); Oct. 25, 2023; 6 pages.

Chart AA-9 Invalidity Contentions: U.S. Pat. No. 11,445,967; Case No. 22-351-CJB (Delaware); Invalidity of U.S. Pat. No. 11,445,967 by U.S. Pat. Pub. No. 2011/0009729 ("Shin"); Oct. 25, 2023; 6 pages.

Chart AA-8 Invalidity Contentions: U.S. Pat. No. 11,445,967; Case No. 22-351-CJB (Delaware); Invalidity of U.S. Pat. No. 11,445,967 by WO 2008/005015 ("Shennib"); Oct. 25, 2023; 6 pages.

Chart AA-7 Invalidity Contentions: U.S. Pat. No. 11,445,967; Case No. 22-351-CJB (Delaware); Invalidity of U.S. Pat. No. 11,445,967 by U.S. Pat. No. 7,206,630 ("Tarler"); Oct. 25, 2023; 7 pages.

Chart AA-6 Invalidity Contentions: U.S. Pat. No. 11,445,967; Case No. 22-351-CJB (Delaware); Invalidity of U.S. Pat. No. 11,445,967 by U.S. Pat. No. 9,669,212 ("Mueller"); Oct. 25, 2023; 6 pages.

Chart AA-5 Invalidity Contentions: U.S. Pat. No. 11,445,967; Case No. 22-351-CJB (Delaware); Invalidity of U.S. Pat. No. 11,445,967 by U.S. Pat. No. 10,413,251 ("Golda"); Oct. 25, 2023; 6 pages.

Chart A-4 Invalidity Contentions: U.S. Pat. No. 11,445,967; Case No. 22-351-CJB (Delaware); Invalidity of U.S. Pat. No. 11,445,967 by U.S. Pat. Pub. No. 2011/0077497 ("Oster"); Oct. 25, 2023; 6 pages.

Chart A-3 Invalidity Contentions: U.S. Pat. No. 11,445,967; Case No. 22-351-CJB (Delaware); Invalidity of U.S. Pat. No. 11,445,967 by U.S. Pat. No. 10,327,660 ("Gallego"); Oct. 25, 2023; 7 pages.

Chart AA-2 Invalidity Contentions: U.S. Pat. No. 11,445,967; Case No. 22-351-CJB (Delaware); Invalidity of U.S. Pat. No. 11,445,967 by U.S. Pat. No. 11,116,447 ("Yang"); Oct. 25, 2023; 14 pages.

(56)    References Cited

OTHER PUBLICATIONS

Chart AA-1 Invalidity Contentions: U.S. Pat. No. 11,445,967; Case No. 22-351-CJB (Delaware); Invalidity of U.S. Pat. No. 11,445,967 by International Publication No. WO 2010/104952 to Mazar ("Mazar"); Oct. 25, 2023; 13 pages.

Chart A-9 Invalidity Contentions: U.S. Pat. No. 11,051,743; Case No. 22-351-CJB (Delaware); Invalidity of U.S. Pat. No. 11,051,743 by U.S. Pat. Pub. No. 2011/0009729 ("Shin"); Oct. 25, 2023; 12 pages.

Chart A-8 Invalidity Contentions: U.S. Pat. No. 11,051,743; Case No. 22-351-CJB (Delaware); Invalidity of U.S. Pat. No. 11,051,743 by WO 2008/005015 ("Shennib"); Oct. 25, 2023; 12 pages.

Chart A-7 Invalidity Contentions: U.S. Pat. No. 11,051,743; Case No. 22-351-CJB (Delaware); Invalidity of U.S. Pat. No. 11,051,743 by U.S. Pat. No. 7,206,630 ("Tarler"); Oct. 25, 2023; 12 pages.

Chart A-6 Invalidity Contentions: U.S. Pat. No. 11,051,743; Case No. 22-351-CJB (Delaware); Invalidity of U.S. Pat. No. 11,051,743 by U.S. Pat. No. 9,669,212 ("Mueller"); Oct. 25, 2023; 11 pages.

Chart A-5 Invalidity Contentions: U.S. Pat. No. 11,051,743; Case No. 22-351-CJB (Delaware); Invalidity of U.S. Pat. No. 11,051,743 by U.S. Pat. No. 10,413,251 ("Golda"); Oct. 25, 2023; 11 pages.

Chart A-4 Invalidity Contentions: U.S. Pat. No. 11,051,743; Case No. 22-351-CJB (Delaware); Invalidity of U.S. Pat. No. 11,051,743 by U.S. Pat. Pub. No. 2011/0077497 ("Oster"); Oct. 25, 2023; 11 pages.

Chart A-2 Invalidity Contentions: U.S. Pat. No. 11,051,743; Case No. 22-351-CJB (Delaware); Invalidity of U.S. Pat. No. 11,051,743 by U.S. Pat. No. 11,116,447 ("Yang"); Oct. 25, 2023; 19 pages.

Chart A-1 Invalidity Contentions: U.S. Pat. No. 11,051,743; Case No. 22-351-CJB (Delaware); Invalidity of U.S. Pat. No. 11,051,743 by International Publication No. WO 2010/104952 to Mazar ("Mazar"); Oct. 25, 2023; 19 pages.

Bardy Diagnostics, Inc., Plaintiff v. Vital Connect, Inc.; The United States District Court for the District of Delaware; C.A. No. 22-351 (CJB); Vitalconnect's Preliminary Invalidity Contentions; filed Oct. 25, 2023.

Wolf, "The Data-Driven Life," New York Times Magazine, Apr. 28, 2010, 13 pages.

Hill, "Adventures in Self-Surveillance: Fitbit, Tracking My Movement and Sleep," Forbes, Feb. 25, 2011, 11 pages.

Mehen, "Open health with the quantified self," Opensource.com, Aug. 25, 2011, 7 pages.

"23 Personal Tools to Learn More About Yourself," Flowingdata.com, Sep. 18, 2008, 18 pages.

Puurtinen et al., "Estimation of ECG Signal of closely separated bipolar electrodes using thorax models," Proceedings of the 26th Annual International Conference of the IEEE EMBS pp. 801-804, San Francisco, Calif., USA, Sep. 1-5, 2004, 4 pages.

Trägårdh et al., How many ECG leads do we need? Cardiol Clin. Aug. 2006;24(3):317-30, vii. doi: 10.1016/j.ccl.2006.04.005. PMID: 16939826; 14 pages.

Adams et al., U.S. Appl. No. 61/755,623, filed Jan. 23, 2013, 48 pages.

Toth et al., U.S. Appl. No. 61/832,131, filed Jun. 6, 2013, 82 pages.

Vishnubhotla, "Pre-processing of ECG signals for ambulatory use," Jan. 2009; 5 pages.

Chaimanonart et al., "A wireless batteryless in vivo EKG and body temperature sensing microsystem with adaptive RF powering for genetically engineered mice monitoring," Jul. 2009; 4 pages.

Alzaidi et al., "Smart Textiles Based Wireless ECG System," May 2012; 5 pages.

Saeed et al., "A Scalable Wireless Body Area Sensor Network for Health-Care Monitoring," Jun. 2009, 4 pages.

Pandian et al., "Wireless Sensor Network for Wearable Physiological Monitoring," Journal of Networks, vol. 3, No. 5, May 2008; 15 pages.

Mukala et al., "A Novel Zigbee-based Low-cost, Low-Power Wireless EKG system," IEEE, May 2010; 4 pages.

Aventyn, Inc., "Vital Connect, Aventyn Launch Wearable Biosensor Platform for Mobile Patient Monitoring", Dec. 12, 2013, 5 pages.

May 2, 2022 Letter From Counsel. 1:22-cv-00351-CFC. May 2, 2022.

Dwayne C. Leonard, A Framework for the Creation of a Unified Electronic Medical Record Using Biometrics, Data Fusion and Belief Theory, 2007, https://dialog.proquest.com/professional/docview/304852676/17AEEF1F9382EF1C4E5/6?accountid=131444 (last visited Aig 27, 2021) (Year: 2007).

May 24, 2022 Letter to Opposing Counsel. 1:22-cv-00351-CFC. May 24, 2022.

Complaint from Case No. 1:22-cv-00351-UNA, Bardy Diagnostics, Inc. (Plaintiff) v. Vital Connect, Inc. (Defendant), Filed: Mar. 18, 2022, 182 pages.

Defendant's Opening Brief in Support of Its Motion to Dismiss for Failure to State a Claim from Case No. 1:22-cv-00351-CFC, Bardy Diagnostics, Inc. (Plaintiff) v. Vital Connect, Inc. (Defendant), Filed: May 25, 2022, 18 pages.

Defendant's Answer, Defenses, and Counterclaim from Case No. 1:22-cv-00351-CFC, Bardy Diagnostics, Inc. (Plaintiff) v. Vital Connect, Inc. (Defendant), Filed: May 25, 2022, 132 pages.

Plaintiff's Answering Brief in Opposition to Defendant's Motion to Dismiss for Failure to State a Claim from Case No. 1:22-cv-00351-CFC, Bardy Diagnostics, Inc. (Plaintiff) v. Vital Connect, Inc. (Defendant), Filed: Jun. 8, 2022, 25 pages.

Plaintiff's Answer to Defendant's Counterclaim from Case No. 1:22-cv-00351-CFC, Bardy Diagnostics, Inc. (Plaintiff) v. Vital Connect, Inc. (Defendant), Filed: Jun. 15, 2022, 5 pages.

Defendant's Reply Brief in Support of Its Motion to Dismiss for Failure to State a Claim from Case No. 1:22-cv-00351-CFC, Bardy Diagnostics, Inc. (Plaintiff) v. Vital Connect, Inc. (Defendant), Filed: Jun. 15, 2022, 93 pages.

Oct. 17, 2022 Letter to Opposing Counsel, Bardy Diagnostics, Inc. v. Vital Connect, Inc., No. 22-cv-00351-CFC (D. Del.), Oct. 17, 2022.

Nov. 11, 2022, Letter from Opposing Counsel, 1:22-cv-00351-CJB; Bardy Diagnostics, Inc. v. Vital Connect, Inc. (D. Del.), Nov. 11, 2022.

Dec. 26, 2022 Letter from Opposing Counsel, 1:22-cv-00351-CJB; Bardy Diagnostics, Inc. v. Vital Connect, Inc. (D. Del.); and IPR2023-00381; Vital Connect, Inc. v. Bardy Diagnostics, Inc. (P.T.A.B.), Dec. 26, 2022.

First Amended Complaint for Patent Infringement, 1:22-cv-00351-CJB, Bardy Diagnostics, Inc. v. Vital Connect, Inc. (D. Del.), filed Jan. 10, 2023.

Petition for Inter Partes Review of U.S. Pat. No. 11,051,743 Pursuant to 35 U.S.C. §§ 311-319 and 37 C.F.R. § 42, Case No. IPR2023-00381, Vital Connect, Inc. v. Bardy Diagnostics, Inc. (P.T.A.B.), Dec. 21, 2022, 875 pages.

G. G. Ivanov, "HRV Analysis Under the Usage of Different Electrocardiopraphy Systems," Apr. 15, 2008 (Apr. 15, 2008), XP55511209, Retrieved from the Internet: URL:http://www.drkucera.eu/upload_doc/hrv_analysis_(methodical_recommendations).pdf [retrieved on Oct. 1, 2018].

Wallot et al., "Using Complexity Metrics With R-R Intervals and BPM Heart Rate Measures," Frontiers in Physiology, vol. 4, Article 211, pp. 1-8, Aug. 13, 2013. 2013.

https://fccid.io/LF524950/User-Manual/User-Manual-1944573 © Medtronic, Inc. 2012.

Dan Sapoznikov et al., "Comparison of Different Methodologies of Heart Rate Variability Analysis," Department of Cardiology, Hadassah University Hospital, P.O.B. 12000, Ein Kerem, Jerusalem 91120, Israel (1993).

Anand et al., "Design of the Multi-Sensor Monitoring in Congestive Heart Failure (MUSIC) Study: Prospective Trial to Assess the Utility of Continuous Wireless Physiologic Monitoring in Heart Failure", Journal of Cardiac Failure, vol. 17, No. 1, Jan. 1, 2011, pp. 11-16 (6 pages).

Cesario et al., "Arrhythmia Detection with a Low-Profile Wireless Adherent Cardiac Monitor: Results from the Adam and Eve Studies", The Journal of Innovations in Cardiac Rhythm Management, 2 (2011) Sep. 2011, pp. 476-482, (7 pages).

(56)         References Cited

OTHER PUBLICATIONS

Corventis Nuvant, "Nuvant Mobile Cardiac Telementry (MTC) System", Corventis, 2009, last printed Jul. 18, 2024, https://web.archive.org/web/20100127193736/http://corventis.com/AP/nuvant.asp.

Corventis Avivo, "Avivo Mobile Patient Management System", Corventis, 2008, lasted printed Jul. 18, 2024, https://web.archive.org/web/20100118155329/http://www.corventis.com/AP/avivo.asp.

IRhythm Zio XT Patch/Event Card, "Zio Patch", iRhythm, 2011, last printed Jul. 18, 2024, https://web.archive.org/web/20111017074139/http://irhythmtech.com/media/files/Z100A4020.04%20-%20ZIO%20PATCH%20DATA%20SHEET.pdf.

*Bardy Diagnostics, Inc.* v. *Vital Connect, Inc.*, Defendant's Identification of Supplemental Prior Art References, C.A. No. 22-351 (CJV), May 22, 2024.

International Preliminary Report on Patentability and Written Opinion, PCT/US2019/064331, Jun. 8, 2021.

First Examination Report, Communication pursuant to Article 94(3) EPC, 19 828 053.9-1113, dated Apr. 15, 2024.

Anand et al., "Design of the Multi-Sensor Monitoring in Congestive Heart Failure (Music) Study: Prospective Trial to Assess the Utility of Continuous Wireless Physiologic Monitoring in Heart Failure", Journal of Cardiac Failure (2011), 17(1), pp. 11-16.

Chart A-10 Invalidity Contentions: U.S. Pat. No. 11,051,743; Case No. 22-351-CJB (Delaware); Invalidity of U.S. Pat. No. 11,051,743 by WO 2003/065926 ("Ozguz"); Oct. 25, 2023; 12 pages.

Chart A-3 Invalidity Contentions: U.S. Pat. No. 11,051,743; Case No. 22-351-CJB (Delaware); Invalidity of U.S. Pat. No. 11,051,743 by U.S. Pat. No. 10,327,660 ("Gallego"); Oct. 25, 2023; 12 pages.

Harland et al., "Electric Potential Probes—New Directions in the Remote Sensing of the Human Body", Measurement Science and Technology (2002), vol. 13, pp. 163-169.

http://www.gtec.at/Products/Software/g. BSanalyze-Specs-Features (2014).

http://www.originlab.com/origin#Data_Exploration 2015.

Invalidity of U.S. Pat. No. 11,051,743 by U.S. Pat. Pub. No. 2011/0077497 ("Oster"); Oct. 25, 2023; 11 pages.

*IRhythm, Inc.*v. *Welch Allyn, Inc.*, Expert Declaration of Jason Heikenfeld for U.S. Pat. Nos. 8,214,007, 8,965,492, 9,155,484, and 10,159,422 dated Dec. 20, 2024. 516 pages.

*IRhythm, Inc.*v. *Welch Allyn, Inc.*, Petition for Inter Partes Review Under 35 U.S.C. § 312 and 37 C.F.R. § 42.104, Case No. IPR2025-00363 for U.S. Pat. No. 10,159,422, dated Dec. 23, 2024. 94 pages.

*IRhythm, Inc.*v. *Welch Allyn, Inc.*, Petition for Inter Partes Review Under 35 U.S.C. § 312 and 37 C.F.R. § 42.104, Case No. IPR2025-00374 for U.S. Pat. No. 8,965,492, dated Dec. 23, 2024. 86 pages.

*IRhythm, Inc.*v. *Welch Allyn, Inc.*, Petition for Inter Partes Review Under 35 U.S.C. § 312 and 37 C.F.R. § 42.104, Case No. IPR2025-00376 for U.S. Pat. No. 9,155,484, dated Dec. 23, 2024. 106 pages.

*IRhythm, Inc.*v. *Welch Allyn, Inc.*, Petition for Inter Partes Review Under 35 U.S.C. § 312 and 37 C.F.R. § 42.104, Case No. IPR2025-00377 for U.S. Pat. No. 8,214,007, dated Dec. 23, 2024. 88 pages.

*IRhythm, Inc.*v. *Welch Allyn, Inc.*, Petition for Inter Partes Review Under 35 U.S.C. § 312 and 37 C.F.R. § 42.104, Case No. IPR2025-00378 for U.S. Pat. No. 8,214,007, dated Dec. 23, 2024. 95 pages.

Knight et al., U.S. Appl. No. 60/786,502, filed Mar. 29, 2006, 8 pages.

*Bardy Diagnostics, Inc.*, Plaintiff v. *iRhythm Technologies, Inc.*; The United States District Court for the District of Delaware; Complaint against iRhythm Technologies; filed Dec. 10, 2024.

Exhibits 1-13 for *Bardy Diagnostics, Inc.*, Plaintiff v. *iRhythm Technologies, Inc.*; The United States District Court for the District of Delaware; Complaint against iRhythm Technologies; filed Dec. 10, 2024.

*Bardy Diagnostics, Inc.*, Plaintiff v. *iRhythm Technologies, Inc.*; The United States District Court for the District of Delaware; C.A. No. 24-1355-RGA; First Amended Complaint against iRhythm Technologies; filed Dec. 26, 2024.

Exhibits 1-15 for *Bardy Diagnostics, Inc.*, Plaintiff v. *iRhythm Technologies, Inc.*; The United States District Court for the District of Delaware; C.A. No. 24-1355-RGA; First Amended Complaint against iRhythm Technologies; filed Dec. 26, 2024.

*Bardy Diagnostics, Inc.*, Plaintiff v. *iRhythm Technologies, Inc.*; The United States District Court for the District of Delaware; C.A. No. 24-1355 (JDW); Defendant iRhythm Technologies, Inc.'s Counterclaim and Answer to Plaintiff Bardy Diagnostics, Inc.'s First Amended Complaint; filed Mar. 3, 2025.

Exhibits 1-10 for *Bardy Diagnostics, Inc.*, Plaintiff v. *iRhythm Technologies, Inc.*; The United States District Court for the District of Delaware; C.A. No. 24-1355 (JDW); Defendant iRhythm Technologies, Inc.'s Counterclaim and Answer to Plaintiff Bardy Diagnostics, Inc.'s First Amended Complaint; filed Mar. 3, 2025.

*Vital Connect, Inc.* v. *Bardy Diagnostics, Inc.*, USPTO Patent Trial & Appeal Board—Patent Owner's Preliminary Response, Case No. IPR2023-00381 for U.S. Pat. No. 11,051,743, dated Apr. 24, 2023. 53 pages.

*Vital Connect, Inc.* v. *Bardy Diagnostics, Inc.*, USPTO Patent Trial & Appeal Board—Decision Denying Institution of Inter Partes Review 35 U.S.C. § 314, Case No. IPR2023-00381 for U.S. Pat. No. 11,051,743, dated Jul. 11, 2023. 21 pages.

*Vital Connect, Inc.* v. *Bardy Diagnostics, Inc.*, USPTO Patent Trial & Appeal Board—Order, Case No. IPR2023-00381 for U.S. Pat. No. 11,051,743, dated Oct. 3, 2023. 3 pages.

*Vital Connect, Inc.* v. *Bardy Diagnostics, Inc.*, USPTO Patent Trial & Appeal Board—Declaration of Dr. Per Reinhall, Ph.D, Case No. IPR2023-00381 for U.S. Pat. No. 11,051,743, dated Apr. 21, 2023. 28 pages.

Bardy Diagnostics Statutory Disclaimer Under 35 U.S.C. 253(a) and 37 C.F.R. § 1.321(a) for U.S. Pat. No. 11,051,743, dated Apr. 21, 2023. 2 pages.

501(k) Summary of Safety & Effectiveness, 501(k) No. K083287, AVIVO Mobile Patient Management System, dated Nov. 6, 2008 ("AVIVO 501(k)").

510(k) Summary of Safety & Effectiveness, 510(k) No. K043604, VivoMetrics, Inc. LifeShirt™ Real-Time, Apr. 29, 2005.

AAMI, Ambulatory Electrocardiographics, ANSI/AAMI EC38:1998 (1998).

AAMI, Cardiac monitors, heart rate meters, and alarms, ANSI/AAMI EC13:2002 (2002).

AAMI, Diagnostic electrocardiographic devices, ANSI/AAMI EC11:1991 (1991).

Ajay Bharadwaj & Umanath Kamath, Accurate ECG signal processing, CA: Cypress Semiconductor (Feb. 2011).

Am. Coll. Cardiology, Am. Heart Ass'n Task Force on Practice Guidelines, ACC/AHA Guidelines for Ambulatory Electrocardiography: Executive Summary and Recommendations, 100 Circulation 886 (1999), available at <https://www.ahajournals.org/doi/full/10.1161/0.

Aoife Morrin et al., Electrochemical Characterization of Commercial and Home-Made Screen-Printed Carbon Electrodes, 36 Anal. Letters, 2021 (2003).

Bert Gyselinckx & Sofie Pollin, Wireless sensor nodes: potential and challenges, Embedded Systems West Conference (2007).

Bert Gyselinckx et al., Human++: Autonomous Wireless Sensors for Body Area Networks, IEEE 2005 Custom Integrated Circuits Conference.

Bert-Uwe Köhler et al., The Principles of Software QRS Detection, IEEE Eng. Med. & Bio. (2002).

Brian Burkhardt, The Future of Electrocardiogramalemetry Systems, Int'l Telemetering Conference Proceedings (2004).

Bruce R. Bowman & Edward Schuck, Medical Instruments and Devices Used in the Home, CRC Press LLC (2000). (Book—Introduction and Preface only)(Full contents available at: https://www.google.com/urlsa=t&rct=j&q=&esrc=s&source=web&cd=&ved=2ahUKEwjwv6b079OPAxVHL9AFHdajHTIQFnoECBwQAQ&url=https%3A%2F%2Fbiblioseb.files.wordpress.com%2F2018%2F03%2Fbiomedical-engineering-handbook-j-d-bronzino.pdf&usg=AOvVaw2egUNjtqQgxyMFMrLNqB2X&opi=89978449).

C.J. Harland et al., Electric Potential Probes—New Directions in the Remote Sensing of the Human Body, 13 Meas. Sci. Tech. 163 (2002).

(56) References Cited

OTHER PUBLICATIONS

Claus F Nielsen et al., Strategic Intelligence Monitor on Personal Health Systems, Phase 2, JR Scientific and Policy Reports, Country Study: Denmark (2013).

Corventis, AVIVO® Mobile Patient Management System, https://corventis.com/US/AVIVO.asp, Dec. 16, 2009 ("AVIVO Webpage").

Corventis, AVIVO™ Mobile Patient Management System, Instructions for Use (2010) ("AVIVO—Instructions for Use").

Creative Materials, Medical Device Specialty Inks and Films, available at <http://www.creativematerials.com/lit-erature/medical_device.pdf>, archived at Wayback Machine (<https://web.archive.org/web/20060508230449/http://www.creativematerials.com/liter.

Daniel E. Becker, Fundamentals of Electrocardiogramterpretation, 53 Anesthesia Progress 53, 53 (2006).

David Prutchi & Michael Norris, Design and Development of Medical Electronic Instrumentation (2005).

Defendant's Preliminary Invalidity Contentions, C.A. No. 1:24-cv-01355-JDW filed Jul. 24, 2025.

Defendant's Answer to First Amended Complaint, Defenses, and Counterclaim, 1 :22-cv-00351-CJB, *Bardy Diagnostics, Inc. v. Vital Connect, Inc.* (D. Del.), filed Jan. 24, 2023 (227 pages).

Devices@FDA: Dexcom STS Continuous Monitors, U.S. Food & Drug Admin. (2005), available at <https://www.accessdata.fda.gov/scripts/cdrh/devicesatfda/index.cfm?db=pma&id=320251>.

Dorthe B. Nielsen et al., Automatic QRS Complex Detection Algorithm Designed for a Novel, Wearable, Wireless Electrocardiogram Recording Device, 34 Ann. Int'l Conf. of the IEEE Embs, San Diego, CA USA, Aug. 28-Sep. 1, 2012.

Edward K. Chung, Ambulatory Electrocardiography Holter Monitor Electrocardiography (1979). (Abstract Only).

Euan A. Ashley & Josef Niebauer, Cardiology Explained (2004), available at <https://www.ncbi.nlm.nih.gov/books/NBK2204/>. (Abstract Only).

Exhibit A: Invalidity of U.S. Pat. No. 12,171,562 by AVIVO ("Corventis AVIVO System"); 4,081 pages.

Exhibit B: Invalidity of U.S. Pat. No. 12,161,473 by the AVIVO System ("Corventis AVIVO System"); 4,322 pages.

Exhibit C: Invalidity of U.S. Pat. No. 12,285,261 by AVIVO ("the Corventis AVIVO System"); 3,049 pages.

Exhibit D: Invalidity of U.S. Pat. No. 12,310,735 by the AVIVO System ("Corventis AVIVO Mobile Patient Management System"); 3,456 pages.

Exhibit E: State of the Art References for U.S. Pat. Nos. 12,161,473, 12,171,562, 12,285,261, and 12,310,735; 11 pages.

F. Lateef et al., The V-Quick patch versus the standard 12-lead ECG system: Time is the essence, International Journal of Emergency Medicine. 1:43-48 (2008).

Gautham Kalahasty et al., A Brief History of Remote Cardiac Monitoring, 5 Cardiac Electrophysiology Clinics 275 (2013).

https://web.archive.org/web/20091216175134/https://corventis.com/US/AVIVO.asp (available at least by Dec. 16, 2009) ("AVIVO Webpage").

*iRhythm, Inc.* v. *Welch Allyn, Inc.*, Petition for Inter Partes Review Under 35 U.S.C. § 312 AND 37 C.F.R. § 42.104, Case No. IPR2025-01081 for U.S. Pat. No. 8,630,699, dated Jun. 3, 2025. 81 pages.

J. Mühlsteff et al., Wearable approach for continuous ECG—and Activity Patient-Monitoring, 1 26th Proc. Int'l Conf. of IEEE Eng'g in Med. & Biol. Soc'y 2184 (2004).

J. Terry Caves et al., Sampled Analog Filtering Using Switched Capacitors as Resistor Equivalents, 12 IEEE Journal of Solid- State Circuits 592 (1977).

Jaehoon Kim, Implanted Antennas for Medical Wireless Communications: Characterizations, Designs and Performance Evaluations (2005) (Ph. D. dissertation, Univ. Cal. L.A.).

Jameco Electronics, 8-Pin, 8-Bit CMOS Microcontrollers Data Sheet, <https://web.archive.org/web/20031126132956/http://jameco.com/Ja meco/Products/ProdDS/200475.pdf> (available as of Nov. 26, 2003).

James Welch, Farzin Guilak, & Steven D. Baker, A Wireless ECH Smart Sensor for Broad Application in Life Threatening Event Detection, Proceedings of the 25th Annual Int'l Conf. of the IEEE EMBS, San Francisco, CA (Sep. 1-5, 2004).

Jan Adamec & Richard Adamec, ECG Holter, Guide to Electrocardiogramarpretation (2008).

Jiapu Pan & Willis J. Tompkins, A Real-Time QRS Detection Algorithm, BME-22 IEEE Transactions on Biomed. Eng'g 230 (1985).

Joel Morganroth, Ambulatory Holter Electrocardiogramaice of Technologies and Clinical Uses, Anals. of Internal. Med. (1985). (Abstract Only).

Klaus-Peter Hoffmann & Roman Ruff, Flexible dry surface- electrodes for ECG long-term monitoring 5739 (2007).

Lawrence R. Dallett & William E. Donaldson, Plastics and Adhesives: A Guide to Their Physical Properties and Uses, U.S. Dep't of Com. (1956).

Linda S. Baas et al., Accuracy of the Precordial V-Quick® Patch in Persons with Cardiac or Pulmonary Disease, 24 The Journal of Emergency Medicine 2, pp. 131-139 (2003). (Abstract Only).

Maeona K. Jacobs, Sources of Measurement Error in Noninvasive Electronic Instrumentation, 13 Nursing Clinics N. Am. 573 (1978).

Majd AlGhatrif & Joseph Lindsay, A Brief Review: History to Understand Fundamentals of Electrocardiograma J. Community Hosp. & Internal Med. Persps. 14383 (2012).

Matts Ahlsén et al., Service-Oriented Middleware Architecture for Mobile Personal Health Monitoring, Int'l Conf. on Wireless Mobile Comm. and Healthcare, Berlin, Heidelberg: Springer Berlin Heidelberg (Oct. 2011).

Medtronic Monitoring Inc., XOH-PIIX, Equipment: Medtronic Monitoring, Inc.,—PIIX; External Photos Report, FCC.report (Feb. 18, 2010), https://fcc.report/FCC-ID/XOH-PIIX/1242847.pdf ("PiiX External").

Medtronic Monitoring Inc., XOH-PIIX, Equipment: Medtronic Monitoring, Inc.,—PIIX; Internal Photos Report, FCC. report (Feb. 18, 2010), https://fcc.report/FCC-ID/XOH-PIIX/1242848.pdf ("PiiX Internal").

Michael R. Neuman, Biopotential Electrodes, Medical Instrumentation (3d ed. 1998).

Mike Cadogan, Norman J. Holter (2022), available at <https://litfl.com/norman-j-holter/>.

N.V. Thakor & J.G Webster, Electrode studies for the long-term ambulatory Ecg, Med. & Biol. Eng. & Comput. (1985). (Abstract Only).

Nihon Kohden, 4 or 8 Patient Telemetry Monitoring, <http://www.nihonkohden.com/products/monitor/wep4200.html>, Oct. 30, 2005 ("Nihon Kohden Webpage—Telemetry Systems").

Nihon Kohden, Patient Monitoring, <http://www.nihonkohden.com/products/monitor/index.html>, Oct. 30, 2005 ("Nihon Kohden Webpage—Overview").

Nihon Kohden, Transmitters for Life Scope monitors, <http://www.nihonkohden.com/products/monitor/transmitters.html>, Oct. 30, 2005 ("Nihon Kohden Webpage—Transmitters").

Nitish V. Thakor, From Holter Monitors to Automatic Defibrillators: Developments in Ambulatory Arrhythmia Monitoring, IEEE Transactions On Biomed. Eng'g, 770 (1984).

Non-Final Office Action from U.S. Appl. No. 18/933,792, mailed Mar. 20, 2025. 27 pages.

P.J.B. Hubner, Which Disposable Chest Electrode?, British Med. J., 507 (Aug. 30, 1969).

Patrick J. Nolan, Sterile Medical Device Package Development, Standard Handbook of Biomedical Eng'g & Design (2004).

R.S. Khandpur, Printed Circuit Boards: Design, Fabrication, Assembly, and Testing (2006).

Robert A. Millikan & E.S. Bishop, Elements of Electricity (1917).

Robert P. Grant, Spatial Vector Electrocardiogramav. 1950).

Roubik Gregorian & William E. Nicholson, Jr., A Switched- Capacitor High-Pass Filter, 27 IEEE Transactions on Circuits and Sys. 226 (1980).

Stephane Donnay, Human++ Wireless Body-area networks (WBAN) for health monitoring applications, ESF Workshop on Wireless Sensor Networks (Apr. 1-2, 2004).

(56)      References Cited

OTHER PUBLICATIONS

Steven L. Higgins, A Novel Patch for Heart Rhythm Monitoring: is the Holter Monitor Obsolete?, Future Cardiology 9:3, 325-333 (2013). (Abstract Only).

Thermo-Electron and VivoMetrics Deliver the First Real-Time Monitoring Ensemble, EMS1, Apr. 10, 2006.

Tilak Shah, Polyurethane Thin-Film Welding for Medical Device Applications, Med. Device and Diagnostic Indus. (2002).

Tsuyoshi Kato et al., An Application of Capacitive Electrode for Detecting Electrocardiogram of Neonates and Infants, 2006 Int'l Conf. of the IEEE Eng'G Med. & Bio. (2006).

TUV Rheinland of North America, Inc., PiiX Emmissions Test Report, Apr. 6, 2009.

V. Trend et al., Are ECG Welsh cup electrodes effectively cleaned?, 14 J. Hosp. Infection 325 (1989).

V.W. Greene, Reuse of Disposable Medical Devices: Historical and Current Aspects, 7 Infection Control & Hosp. Epidemiology 508 (1986). (Abstract Only).

VPMS Components, V Patch Medical Systems—Next generation Wireless ECG Telemetry, https://www.vpatchmedical.com/pages/vpms-components.php (Jan. 14, 2011).

Zeli Gao, et al., Design of ECG signal acquisition and processing system, 2012 International Conference On Biomedical Engineering and Biotechnology, IEEE, 2012, 762.

Biospace.com, "Proteus Biomedical, Inc. Raises $25M; Gets FDA 510(k) Clearance for Raisin Personal Monitor", BioSpace, URL: <https://www.biospace.com>. (Apr. 21, 2010). 8 pages.

Catherwood et al., "ECG Motion Artefact Reduction Improvements of a Chest-Based Wireless Patient Monitoring System", Computing in Cardiology (2010), vol. 37, pp. 557-560.

Dolan, Brian, "Isansys Secures CE Mark for Wearable Wireless Medical Sensor", MobiHealth News, (Apr. 18, 2012). 15 pages.

McAdams et al., "Wearable Sensor Systems: The Challenges", 33rd Annual International Conference of the IEEE in Medicine and Biology Society (2011), Boston, Massachusetts, pp. 3648-3651.

ACLS Medical Training, The Basics of ECG, available at <https://www.aclsmedicaltraining.com/basics-of-ecg/>.

Cledo Brunetti and Roger Curtis, Proceedings of the I.R.E.—Waves and Electrons Section, Printed-Circuit Techniques (1948).

Copy of Statutory Disclaimer of U.S. Pat. No. 9,155,484, filed Apr. 7, 2025.

File History of U.S. Pat. No. 8,214,007.

File History of U.S. Pat. No. 8,750,974.

Lisleapex, PIC12C508-04/SM, Microchip Technology, available at <https://www.lisleapex.com/product-pic12c508t-04-sm>. Screenshot retrieved Apr. 22, 2026.

NLM, In Brief: What is an electrocardiogram (ECG)?, available at <https://www.ncbi.nlm.nih.gov/books/NBK536878/>.

Roger A. Freedman & Hugh D. Young, University Physics 15th ed. (2019).

Texas Instruments, Wave Digital Filtering Using an MSP430™ MCU, available at: <https://www.ti.com/lit/pdf/slaa331#:~:text=FIR%20filter%implementation%20in%20an, performance%20and%20fast%20execution%20times>.

*Welch Allyn, Inc.* v. *iRhythm Techs., Inc.*, C.A. No. 24-224-MN; Amended Joint Claim Construction Chart (DDE Jan. 29, 2026) (excerpted).

*Welch Allyn, Inc.* v. *iRhythm Techs., Inc.*, C.A. No. 24-224-MN; Welch Allyn, Inc.'s Opening Markman Brief (DDE Feb. 5, 2026).

ELECTROCARDIOGRAPHY PATCH

FIELD

This application relates in general to electrocardiographic monitoring and, in particular, to an electrocardiography patch.

BACKGROUND

The heart emits electrical signals as a by-product of the propagation of the action potentials that trigger depolarization of heart fibers. An electrocardiogram (ECG) measures and records such electrical potentials to visually depict the electrical activity of the heart over time. Conventionally, a standardized set format 12-lead configuration is used by an ECG machine to record cardiac electrical signals from well-established traditional chest locations. Electrodes at the end of each lead are placed on the skin over the anterior thoracic region of the patient's body to the lower right and to the lower left of the sternum, on the left anterior chest, and on the limbs. Sensed cardiac electrical activity is represented by PQRSTU waveforms that can be interpreted post-ECG recordation to derive heart rate and physiology. The P-wave represents atrial electrical activity. The QRSTU components represent ventricular electrical activity.

An ECG is a tool used by physicians to diagnose heart problems and other potential health concerns. An ECG is a snapshot of heart function, typically recorded over 12 seconds, that can help diagnose rate and regularity of heartbeats, effect of drugs or cardiac devices, including pacemakers and implantable cardioverter-defibrillators (ICDs), and whether a patient has heart disease. ECGs are used in-clinic during appointments, and, as a result, are limited to recording only those heart-related aspects present at the time of recording. Sporadic conditions that may not show up during a spot ECG recording require other means to diagnose them. These disorders include fainting or syncope; rhythm disorders, such as tachyarrhythmias and bradyarrhythmias; apneic episodes; and other cardiac and related disorders. Thus, an ECG only provides a partial picture and can be insufficient for complete patient diagnosis of many cardiac disorders.

Diagnostic efficacy can be improved, when appropriate, through the use of long-term extended ECG monitoring. Recording sufficient ECG and related physiology over an extended period is challenging, and often essential to enabling a physician to identify events of potential concern. A 30-day observation day period is considered the "gold standard" of ECG monitoring, yet achieving a 30-day observation day period has proven unworkable because such ECG monitoring systems are arduous to employ, cumbersome to the patient, and excessively costly. Ambulatory monitoring in-clinic is implausible and impracticable. Nevertheless, if a patient's ECG could be recorded in an ambulatory setting, thereby allowing the patient to engage in activities of daily living, the chances of acquiring meaningful information and capturing an abnormal event while the patient is engaged in normal activities becomes more likely to be achieved.

For instance, the long-term wear of ECG electrodes is complicated by skin irritation and the inability ECG electrodes to maintain continual skin contact after a day or two. Moreover, time, dirt, moisture, and other environmental contaminants, as well as perspiration, skin oil, and dead skin cells from the patient's body, can get between an ECG electrode, the non-conductive adhesive used to adhere the ECG electrode, and the skin's surface. All of these factors adversely affect electrode adhesion and the quality of cardiac signal recordings. Furthermore, the physical movements of the patient and their clothing impart various compressional, tensile, and torsional forces on the contact point of an ECG electrode, especially over long recording times, and an inflexibly fastened ECG electrode will be prone to becoming dislodged. Moreover, dislodgment may occur unbeknownst to the patient, making the ECG recordings worthless. Further, some patients may have skin that is susceptible to itching or irritation, and the wearing of ECG electrodes can aggravate such skin conditions. Thus, a patient may want or need to periodically remove or replace ECG electrodes during a long-term ECG monitoring period, whether to replace a dislodged electrode, reestablish better adhesion, alleviate itching or irritation, allow for cleansing of the skin, allow for showering and exercise, or for other purpose. Such replacement or slight alteration in electrode location actually facilitates the goal of recording the ECG signal for long periods of time.

Conventionally, Holter monitors are widely used for long-term extended ECG monitoring. Typically, they are often used for only 24-48 hours. A typical Holter monitor is a wearable and portable version of an ECG that include cables for each electrode placed on the skin and a separate battery-powered ECG recorder. The cable and electrode combination (or leads) are placed in the anterior thoracic region in a manner similar to what is done with an in-clinic standard ECG machine. The duration of a Holter monitoring recording depends on the sensing and storage capabilities of the monitor, as well as battery life. A "looping" Holter (or event) monitor can operate for a longer period of time by overwriting older ECG tracings, thence "recycling" storage in favor of extended operation, yet at the risk of losing event data. Although capable of extended ECG monitoring, Holter monitors are cumbersome, expensive and typically only available by medical prescription, which limits their usability. Further, the skill required to properly place the electrodes on the patient's chest hinders or precludes a patient from replacing or removing the precordial leads and usually involves moving the patient from the physician office to a specialized center within the hospital or clinic.

The ZIO XT Patch and ZIO Event Card devices, manufactured by iRhythm Tech., Inc., San Francisco, CA, are wearable stick-on monitoring devices that are typically worn on the upper left pectoral region to respectively provide continuous and looping ECG recording. The location is used to simulate surgically implanted monitors. Both of these devices are prescription-only and for single patient use. The ZIO XT Patch device is limited to a 14-day monitoring period, while the electrodes only of the ZIO Event Card device can be worn for up to 30 days. The ZIO XT Patch device combines both electronic recordation components and physical electrodes into a unitary assembly that adheres to the patient's skin. The ZIO XT Patch device uses adhesive sufficiently strong to support the weight of both the monitor and the electrodes over an extended period of time and to resist disadherance from the patient's body, albeit at the cost of disallowing removal or relocation during the monitoring period. The ZIO Event Card device is a form of downsized Holter monitor with a recorder component that must be removed temporarily during baths or other activities that could damage the non-waterproof electronics. Both devices represent compromises between length of wear and quality of ECG monitoring, especially with respect to ease of long term use, female-friendly fit, and quality of atrial (P-wave) signals.

Therefore, a need remains for an extended wear continuously recording ECG monitor practicably capable of being worn for a long period of time, especially in women where breast anatomy can interfere with signal quality in both men and women and capable of recording atrial signals reliably.

A further need remains for a device capable of recording signals ideal for arrhythmia discrimination, especially a device designed for atrial activity recording.

SUMMARY

Physiological monitoring can be provided through a wearable monitor that includes two components, a flexible extended wear electrode patch and a removable reusable monitor recorder. The wearable monitor sits centrally (in the midline) on the patient's chest along the sternum oriented top-to-bottom. The placement of the wearable monitor in a location at the sternal midline (or immediately to either side of the sternum), with its unique narrow "hourglass"-like shape, significantly improves the ability of the wearable monitor to cutaneously sense cardiac electric signals, particularly the P-wave (or atrial activity) and, to a lesser extent, the QRS interval signals in the ECG waveforms indicating ventricular activity. The electrode patch is shaped to fit comfortably and conformal to the contours of the patient's chest approximately centered on the sternal midline. To counter the dislodgment due to compressional and torsional forces, a layer of non-irritating adhesive, such as hydrocolloid, is provided at least partially on the underside, or contact, surface of the electrode patch, but only on the electrode patch's distal and proximal ends. To counter dislodgment due to tensile and torsional forces, a strain relief is defined in the electrode patch's flexible circuit using cutouts partially extending transversely from each opposite side of the flexible circuit and continuing longitudinally towards each other to define in 'S'-shaped pattern. Each of these components are distinctive and allow for comfortable and extended wear, especially by women, where breast mobility would otherwise interfere with monitor use and comfort.

One embodiment provides an extended wear electrocardiography patch. A flexible backing is formed of an elongated strip of stretchable material with a narrow longitudinal midsection evenly tapering inward from both ends. The elongated strip is adherable only on each end of a contact surface to serve as a crimp relief to facilitate compression of the narrow longitudinal midsection in response to compressional and torsional forces. A pair of electrocardiographic electrodes is respectively affixed to and conductively exposed on the contact surface of each end of the elongated strip. A flexible circuit is affixed on each end to the elongated strip. The flexible circuit includes a pair of circuit traces both originating within one of the ends of the elongated strip and which are electrically coupled to each electrocardiographic electrode. A laterally-extendable strain relief is defined in the flexible circuit and formed to facilitate extension and rotation of the flexible circuit in response to tensile and torsional forces. A non-conductive receptacle is securely adhered on the one end of the elongated strip opposite the contact surface and is formed to removably receive an electrocardiography monitor. The non-conductive receptacle includes electrode terminals aligned to electrically interface the pair of circuit traces to the electrocardiography monitor.

A further embodiment provides an electrocardiography patch. A backing has an elongated strip with a midsection connecting two rounded ends. The midsection tapers in from each of the rounded ends and is narrower than each of the two rounded ends. Each electrode, of a pair of electrodes, is positioned on one of the rounded ends of the backing, on a contact surface, to capture electrocardiographic signals. A flex circuit is coupled to each of the electrodes. A non-conductive receptacle is affixed on an outer surface of the backing, opposite the contact surface. Electrical contacts are provided on a surface of the non-conductive receptacle opposite the backing. A battery is provided on the outer surface of the backing and a processor is powered by the battery to write the electrocardiographic signals into memory.

The monitoring patch is especially suited to the female anatomy. The narrow longitudinal midsection can fit nicely within the intermammary cleft of the breasts without inducing discomfort, whereas conventional patch electrodes are wide and, if adhesed between the breasts, would cause chafing, irritation, frustration, and annoyance, leading to low patient compliance.

The foregoing aspects enhance ECG monitoring performance and quality facilitating long-term ECG recording, critical to accurate arrhythmia diagnosis.

In addition, the foregoing aspects enhance comfort in women (and certain men), but not irritation of the breasts, by placing the monitoring patch in the best location possible for optimizing the recording of cardiac signals from the atrium, another feature critical to proper arrhythmia diagnosis.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

DETAILED DESCRIPTION

Figure 1:
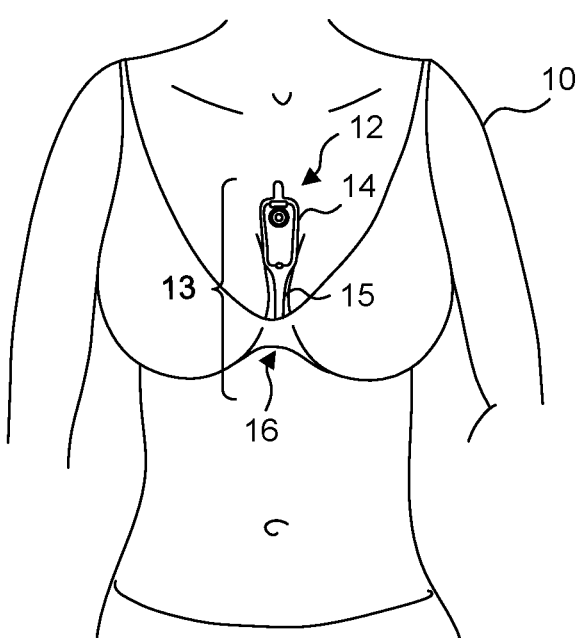
FIGS. 1 and 2 are diagrams showing, by way of examples, an extended wear electrocardiography monitor, including an extended wear electrode patch in accordance with one embodiment, respectively fitted to the sternal region of a female patient and a male patient.
Figure 2:
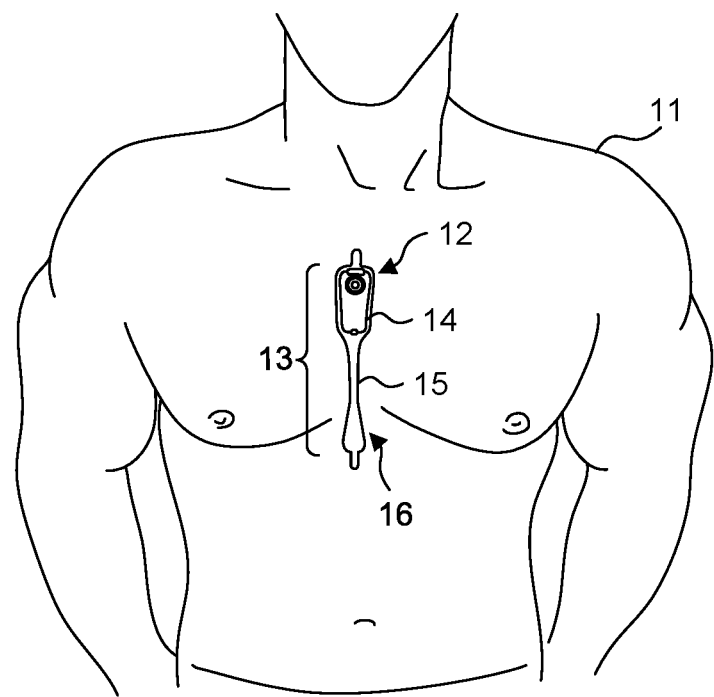

Physiological monitoring can be provided through a wearable monitor that includes two components, a flexible extended wear electrode patch and a removable reusable monitor recorder. FIGS. 1 and 2 are diagrams showing, by way of examples, an extended wear electrocardiography monitor 12, including an extended wear electrode patch 15 in accordance with one embodiment, respectively fitted to the sternal region of a female patient 10 and a male patient 11. The wearable monitor 12 sits centrally (in the midline) on the patient's chest along the sternum 13 oriented top-to-bottom with the monitor recorder 14 preferably situated towards the patient's head. The electrode patch 15 is shaped to fit comfortably and conformal to the contours of the patient's chest approximately centered on the sternal midline 16 (or immediately to either side of the sternum 13). The distal end of the electrode patch 15 extends towards the Xiphoid process and, depending upon the patient's build, may straddle the region over the Xiphoid process. The proximal end of the electrode patch 15, located under the monitor recorder 14, is below the manubrium and, depending upon patient's build, may straddle the region over the manubrium.

The placement of the wearable monitor 12 in a location at the sternal midline 16 (or immediately to either side of the sternum 13) significantly improves the ability of the wearable monitor 12 to cutaneously sense cardiac electric signals, particularly the P-wave (or atrial activity) and, to a lesser extent, the QRS interval signals in the ECG waveforms that indicate ventricular activity. The sternum 13 overlies the right atrium of the heart and the placement of the wearable monitor 12 in the region of the sternal midline 13 puts the ECG electrodes of the electrode patch 15 in a location better adapted to sensing and recording P-wave signals than other placement locations, say, the upper left pectoral region. In addition, placing the lower or inferior pole (ECG electrode) of the electrode patch 15 over (or near) the Xiphoid process facilitates sensing of right ventricular activity and provides superior recordation of the QRS interval.

Figure 3:
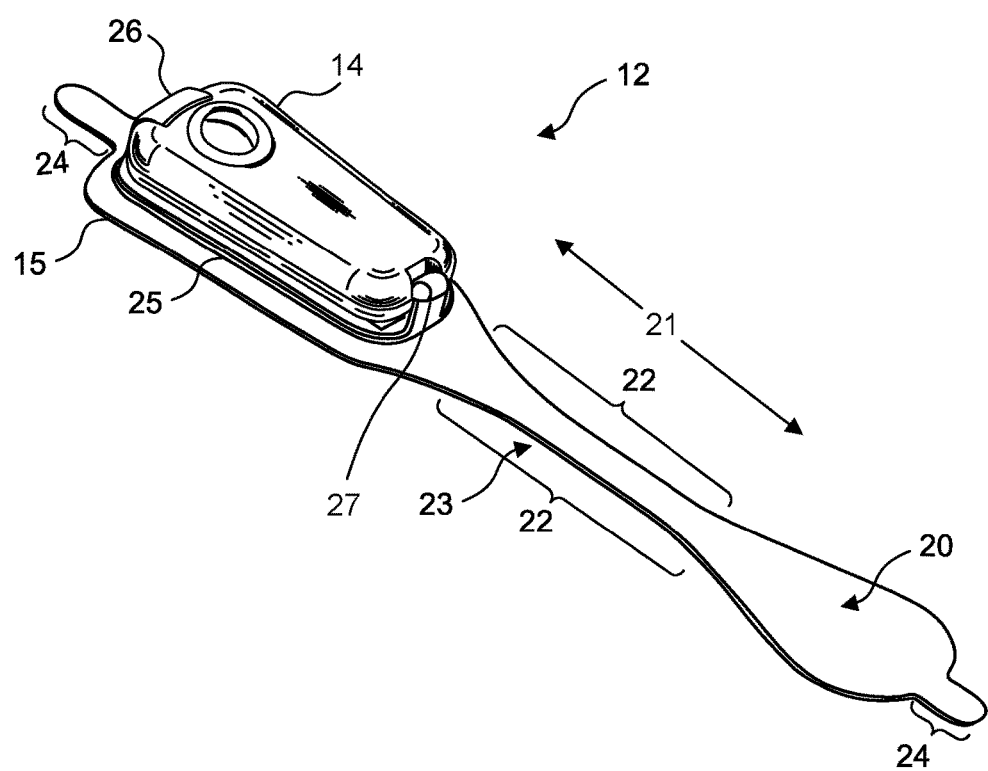
FIG. 3 is a perspective view showing an extended wear electrode patch in accordance with one embodiment with a monitor recorder inserted.

During use, the electrode patch 15 is first adhesed to the skin along the sternal midline 16 (or immediately to either side of the sternum 13). A monitor recorder 14 is then snapped into place on the electrode patch 15 to initiate ECG monitoring. FIG. 3 is a perspective view showing an extended wear electrode patch 15 in accordance with one embodiment with a monitor recorder 14 inserted. The body of the electrode patch 15 is preferably constructed using a flexible backing 20 formed as an elongated strip 21 of wrap knit or similar stretchable material about 145 mm long and 32 mm at the widest point with a narrow longitudinal mid-section 23 evenly tapering inward from both sides. A pair of cut-outs 22 between the distal and proximal ends of the electrode patch 15 create a narrow longitudinal midsection 23 or "isthmus" and defines an elongated "hourglass"-like shape, when viewed from above, such as described in commonly-assigned U.S. Design Pat. No. D744659, issued Dec. 1, 2015, the disclosure of which is incorporated by reference. The upper part of the "hourglass" is sized to allow an electrically non-conductive receptacle 25, sits on top of the outward-facing surface of the electrode patch 15, to be affixed to the electrode patch 15 with an ECG electrode placed underneath on the patient-facing underside, or contact, surface of the electrode patch 15; the upper part of the "hourglass" has a longer and wider profile than the lower part of the "hourglass," which is sized primarily to allow just the placement of an ECG electrode.

The electrode patch 15 incorporates features that significantly improve wearability, performance, and patient comfort throughout an extended monitoring period. During wear, the electrode patch 15 is susceptible to pushing, pulling, and torqueing movements, including compressional and torsional forces when the patient bends forward, and tensile and torsional forces when the patient leans backwards. To counter these stress forces, the electrode patch 15 incorporates crimp and strain reliefs, as further described infra respectively with reference to FIGS. 4 and 5. In addition, the cut-outs 22 and longitudinal midsection 23 help minimize interference with and discomfort to breast tissue, particularly in women (and gynecomastic men). The cut-outs 22 and longitudinal midsection 23 allow better conformity of the electrode patch 15 to sternal bowing and to the narrow isthmus of flat skin that can occur along the bottom of the intermammary cleft between the breasts, especially in buxom women. The cut-outs 22 and longitudinal midsection 23 help the electrode patch 15 fit nicely between a pair of female breasts in the intermammary cleft. In one embodiment, the cut-outs 22 can be graduated to form the longitudinal midsection 23 as a narrow in-between stem or isthmus portion about 7 mm wide. In a still further embodiment, tabs 24 can respectively extend an additional 8 mm to 12 mm beyond the distal and proximal ends of the flexible backing 20 to facilitate purchase when adhering the electrode patch 15 to or removing the electrode patch 15 from the sternum 13. These tabs preferably lack adhesive on the underside, or contact, surface of the electrode patch 15. Still other shapes, cut-outs and conformities to the electrode patch 15 are possible.

The monitor recorder 14 removably and reusably snaps into an electrically non-conductive receptacle 25 during use. The monitor recorder 14 contains electronic circuitry for recording and storing the patient's electrocardiography as sensed via a pair of ECG electrodes provided on the electrode patch 15, such as described in commonly-assigned U.S. Pat. No. 9,730,593, issued Aug. 15, 2017, the disclosure of which is incorporated by reference. The circuitry includes a microcontroller, storage, ECG signal processing, analog-to-digital conversion (where applicable), and an external interface for coupling to the electrode patch 15 and to a download station for stored data download and device programming. The monitor recorder 14 also includes external patient-interfaceable controls, such as a push button to facilitate event marking and a resonance circuit to provide vibratory output. In a further embodiment, the circuitry, with the assistance of the appropriate types of deployed electrodes or sensors, is capable of monitoring other types of physiology, in addition to ECGs. Still other types of monitor recorder components and functionality are possible.

The non-conductive receptacle 25 is provided on the top surface of the flexible backing 20 with a retention catch 26 and tension clip 27 molded into the non-conductive receptacle 25 to conformably receive and securely hold the monitor recorder 14 in place. The edges of the bottom surface of the non-conductive receptacle 25 are preferably rounded, and the monitor recorder 14 is nestled inside the interior of the non-conductive receptacle 25 to present a rounded (gentle) surface, rather than a sharp edge at the skin-to-device interface.

The electrode patch 15 is intended to be disposable. The monitor recorder 14, however, is reusable and can be transferred to successive electrode patches 15 to ensure continuity of monitoring. The placement of the wearable monitor 12 in a location at the sternal midline 16 (or immediately to either side of the sternum 13) benefits long-term extended wear by removing the requirement that ECG electrodes be continually placed in the same spots on the skin throughout the monitoring period. Instead, the patient is free to place an electrode patch 15 anywhere within the general region of the sternum 13.

As a result, at any point during ECG monitoring, the patient's skin is able to recover from the wearing of an electrode patch 15, which increases patient comfort and satisfaction, while the monitor recorder 14 ensures ECG monitoring continuity with minimal effort. A monitor recorder 14 is merely unsnapped from a worn out electrode patch 15, the worn out electrode patch 15 is removed from the skin, a new electrode patch 15 is adhered to the skin, possibly in a new spot immediately adjacent to the earlier location, and the same monitor recorder 14 is snapped into the new electrode patch 15 to reinitiate and continue the ECG monitoring.

Figure 4:
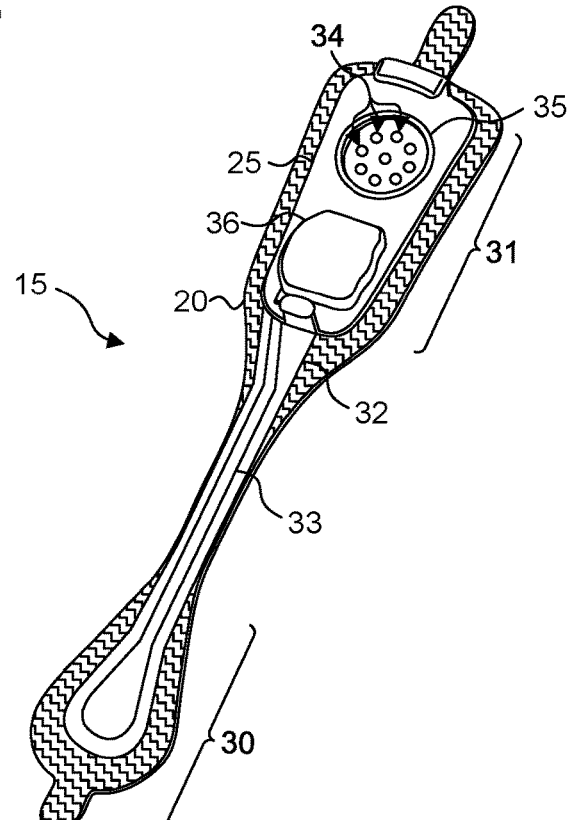
FIG. 4 is a perspective view showing the extended wear electrode patch of FIG. 3 without a monitor recorder inserted.

During use, the electrode patch 15 is first adhered to the skin in the sternal region. FIG. 4 is a perspective view showing the extended wear electrode patch 15 of FIG. 3 without a monitor recorder 14 inserted. A flexible circuit 32 is adhered to each end of the flexible backing 20. A distal circuit trace 33 from the distal end 30 of the flexible backing 20 and a proximal circuit trace (not shown) from the proximal end 31 of the flexible backing 20 electrically couple ECG electrodes (not shown) to a pair of electrical pads 34. The electrical pads 34 are provided within a moisture-resistant seal 35 formed on the bottom surface of the non-conductive receptacle 25. When the monitor recorder 14 is securely received into the non-conductive receptacle 25, that is, snapped into place, the electrical pads 34 interface to electrical contacts (not shown) protruding from the bottom surface of the monitor recorder 14, and the moisture-resistant seal 35 enables the monitor recorder 14 to be worn at all times, even during bathing or other activities that could expose the monitor recorder 14 to moisture.

In addition, a battery compartment 36 is formed on the bottom surface of the non-conductive receptacle 25, and a pair of battery leads (not shown) electrically interface the battery to another pair of the electrical pads 34. The battery contained within the battery compartment 35 can be replaceable, rechargeable or disposable.

The monitor recorder 14 draws power externally from the battery provided in the non-conductive receptacle 25, thereby uniquely obviating the need for the monitor recorder 14 to carry a dedicated power source. The battery contained within the battery compartment 35 can be replaceable, rechargeable or disposable. In a further embodiment, the ECG sensing circuitry of the monitor recorder 14 can be supplemented with additional sensors, including an SpO2 sensor, a blood pressure sensor, a temperature sensor, respiratory rate sensor, a glucose sensor, an air flow sensor, and a volumetric pressure sensor, which can be incorporated directly into the monitor recorder 14 or onto the non-conductive receptacle 25.

The placement of the flexible backing 20 on the sternal midline 16 (or immediately to either side of the sternum 13) also helps to minimize the side-to-side movement of the wearable monitor 12 in the left- and right-handed directions during wear. However, the wearable monitor 12 is still susceptible to pushing, pulling, and torqueing movements, including compressional and torsional forces when the patient bends forward, and tensile and torsional forces when the patient leans backwards. To counter the dislodgment of the flexible backing 20 due to compressional and torsional forces, a layer of non-irritating adhesive, such as hydrocolloid, is provided at least partially on the underside, or contact, surface of the flexible backing 20, but only on the distal end 30 and the proximal end 31. As a result, the underside, or contact surface of the longitudinal midsection 23 does not have an adhesive layer and remains free to move relative to the skin. Thus, the longitudinal midsection 23 forms a crimp relief that respectively facilitates compression and twisting of the flexible backing 20 in response to compressional and torsional forces. Other forms of flexible backing crimp reliefs are possible.

Figure 5:
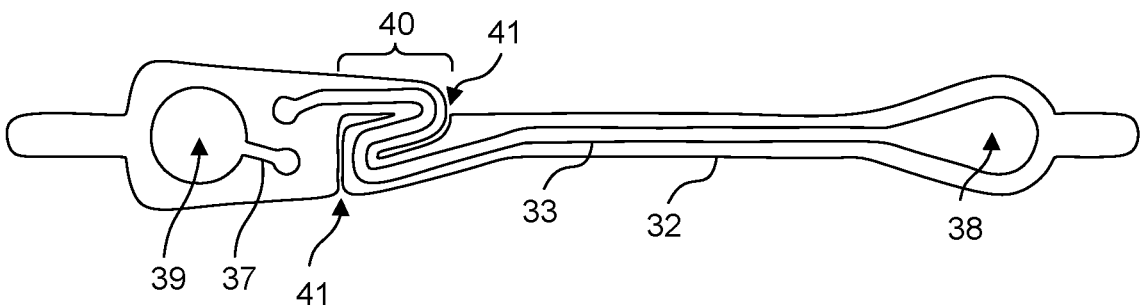
FIG. 5 is a top view showing the flexible circuit of the extended wear electrode patch of FIG. 3.

Unlike the flexible backing 20, the flexible circuit 32 is only able to bend and cannot stretch in a planar direction. FIG. 5 is a top view showing the flexible circuit 32 of the extended wear electrode patch 15 of FIG. 3. A distal ECG electrode 38 and proximal ECG electrode 39 are respectively coupled to the distal and proximal ends of the flexible circuit 32. The flexible circuit 32 preferably does not extend to the outside edges of the flexible backing 20, thereby avoiding gouging or discomforting the patient's skin during extended wear, such as when sleeping on the side. During wear, the ECG electrodes 38, 39 must remain in continual contact with the skin. A strain relief 40 is defined in the flexible circuit 32 at a location that is partially underneath the battery compartment 36 when the flexible circuit 32 is affixed to the flexible backing 20. The strain relief 40 is laterally extendable to counter dislodgment of the ECG electrodes 38, 39 due to tensile and torsional forces. A pair of strain relief cutouts 41 partially extend transversely from each opposite side of the flexible circuit 32 and continue longitudinally towards each other to define in 'S'-shaped pattern, when viewed from above. The strain relief respectively facilitates longitudinal extension and twisting of the flexible circuit 32 in response to tensile and torsional forces. Other forms of circuit board strain relief are possible.

Figure 6:
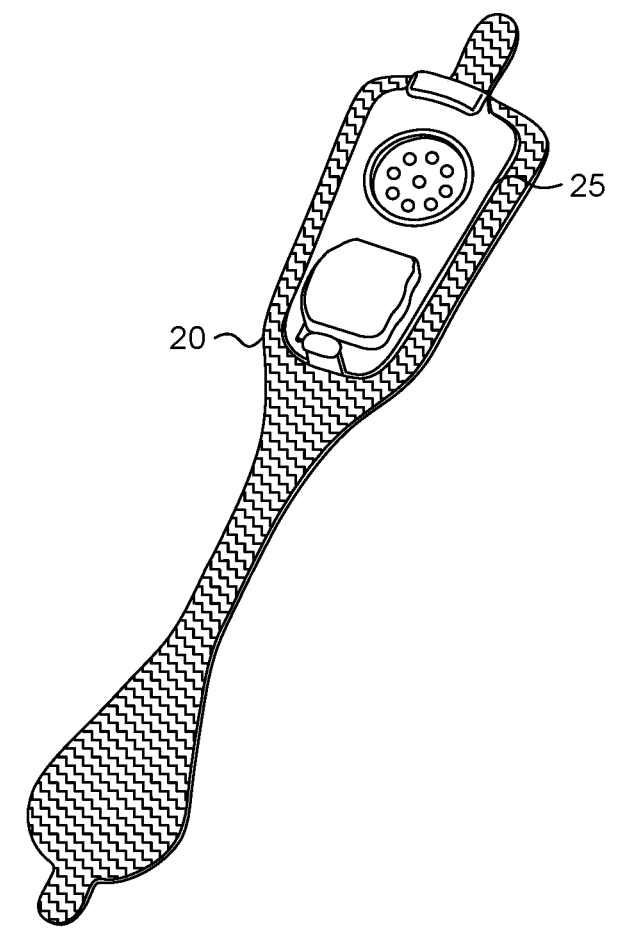
FIG. 6 is a perspective view showing the extended wear electrode patch in accordance with a further embodiment.

The flexible circuit 32 can be provided either above or below the flexible backing 20. FIG. 6 is a perspective view showing the extended wear electrode patch 15 in accordance with a further embodiment. The flexible circuit (not shown) is provided on the underside, or contact, surface of the flexible backing 20 and is electrically interfaced to the set of electrical pads 34 on the bottom surface of the non-conductive receptacle 25 through electrical contacts (not shown) pierced through the flexible backing 20.

Figure 7:
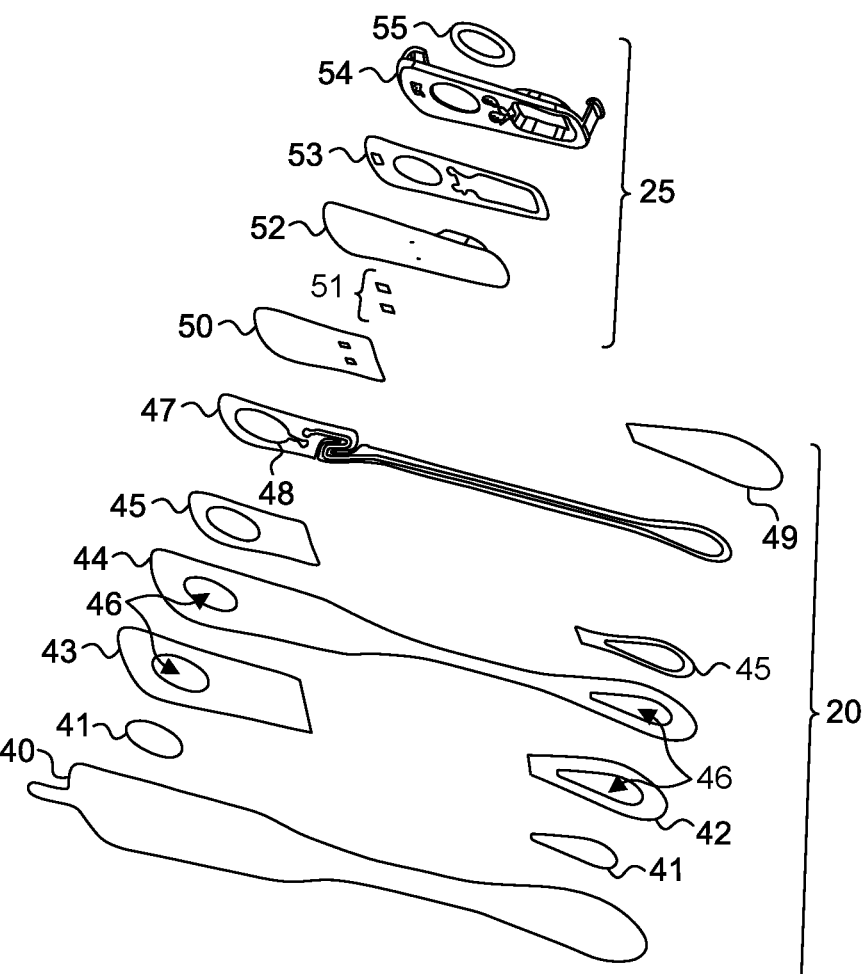
FIG. 7 is an exploded view showing the component layers of the electrode patch of FIG. 3.

The electrode patch 15 is intended to be a disposable component, which enables a patient to replace the electrode patch 15 as needed throughout the monitoring period, while maintaining continuity of physiological sensing through reuse of the same monitor recorder 14. FIG. 7 is an exploded view showing the component layers of the electrode patch 15 of FIG. 3. The flexible backing 20 is constructed of a wearable gauze, latex, or similar wrap knit or stretchable and wear-safe material 44, such as a Tricot-type linen with a pressure sensitive adhesive (PSA) on the underside, or contact, surface. The wearable material 44 is coated with a layer 43 of non-irritating adhesive, such as hydrocolloid, to facilitate long-term wear. The hydrocolloid, for instance, is typically made of mineral oil, cellulose and water and lacks any chemical solvents, so should cause little itching or irritation. Moreover, hydrocolloid is thicker and more gel-like than most forms of PSA and provides cushioning between the relatively rigid and unyielding non-conductive receptacle 25 and the patient's skin. In a further embodiment, the layer of non-irritating adhesive can be contoured, such as by forming the adhesive with a concave or convex cross-section; surfaced, such as through stripes or cross-hatches of adhesive, or by forming dimples in the adhesive's surface; or applied discontinuously, such as with a formation of discrete dots of adhesive.

As described supra with reference to FIG. 5, a flexible circuit can be adhered to either the outward facing surface or the underside, or contact, surface of the flexible backing 20. For convenience, a flexible circuit 47 is shown relative to the outward facing surface of the wearable material 44 and is adhered respectively on a distal end by a distal electrode seal 45 and on a proximal end by a proximal electrode seal 45.

In a further embodiment, the flexible circuit 47 can be provided on the underside, or contact, surface of the wearable material 44. Through the electrode seals, only the distal and proximal ends of the flexible circuit 47 are attached to the wearable material 44, which enables the strain relief 40 (shown in FIG. 5) to respectively longitudinally extend and twist in response to tensile and torsional forces during wear. Similarly, the layer 43 of non-irritating adhesive is provided on the underside, or contact, surface of the wearable material 44 only on the proximal and distal ends, which enables the longitudinal midsection 23 (shown in FIG. 3) to respectively bow outward and away from the sternum 13 or twist in response to compressional and torsional forces during wear.

Figure 8:
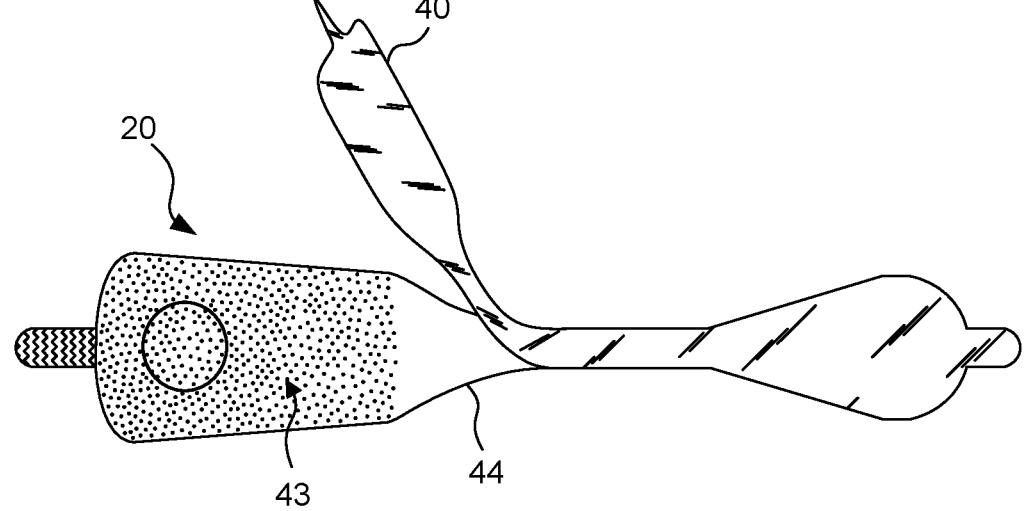
FIG. 8 is a bottom plan view of the extended wear electrode patch of FIG. 3 with liner partially peeled back.

A pair of openings 46 is defined on the distal and proximal ends of the wearable material 44 and layer 43 of non-irritating adhesive for ECG electrodes 38, 39 (shown in FIG. 5). The openings 46 serve as "gel" wells with a layer of hydrogel 41 being used to fill the bottom of each opening 46 as a conductive material that aids electrode signal pick up. The entire underside, or contact, surface of the flexible backing 20 is protected prior to use by a liner layer 40 that is peeled away, as shown in FIG. 8.

The non-conductive receptacle 25 includes a main body 54 that is molded out of polycarbonate, ABS, or an alloy of those two materials to provide a high surface energy to facilitate adhesion of an adhesive seal 53. The main body 54 is attached to a battery printed circuit board 52 by the adhesive seal 53 and, in turn, the battery printed circuit board 52 is adhesed to the flexible circuit 47 with an upper flexible circuit seal 50. A pair of conductive transfer adhesive points 51 or, alternatively, metallic rivets or similar conductive and structurally unifying components, connect the circuit traces 33, 37 (shown in FIG. 5) of the flexible circuit 47 to the battery printed circuit board 52. The main body 54 has a retention catch 26 and tension clip 27 (shown in FIG. 3) that fixably and securely receive a monitor recorder 14 (not shown), and includes a recess within which to circumferentially receive a die cut gasket 55, either rubber, urethane foam, or similar suitable material, to provide a moisture resistant seal to the set of pads 34.

While the invention has been particularly shown and described as referenced to the embodiments thereof, those skilled in the art will understand that the foregoing and other changes in form and detail may be made therein without departing from the spirit and scope.

What is claimed is:

1. An electrocardiography patch, comprising:
   a backing comprising an elongated strip with a midsection connecting two rounded ends, wherein the midsection tapers in from each of the rounded ends and is narrower than each of the two rounded ends;
   a pair of electrodes, each electrode positioned on one of the rounded ends of the backing on a contact surface to capture electrocardiographic signals;
   a flex circuit coupled to each of the electrodes;
   a non-conductive receptacle affixed to the backing and operable to removably receive an electrocardiography monitor, the non-conductive receptacle comprising:
      electrical contacts, wherein the electrical contacts are provided on a surface opposite the backing;
      a compartment; and
      a battery disposed within the compartment;
   a processor powered by the battery to write the electrocardiographic signals into memory; and
   a layer configured to protect the backing prior to application on a patient.

2. The electrocardiography patch according to claim 1, wherein the battery is one of rechargeable, replaceable, and disposable.

3. The electrocardiography patch according to claim 1, further comprising:
   adhesive coating at least a portion of the contact surface of the backing.

4. The electrocardiography patch according to claim 3, wherein the adhesive coats the two rounded ends of the backing on the contact surface.

5. The electrocardiography patch according to claim 1, wherein the adhesive comprises hydrocolloid.

6. The electrocardiography patch according to claim 1, wherein the two rounded ends of the backing are different shapes.

7. The electrocardiography patch according to claim 1, wherein the backing extends beyond the flex circuit.

8. The electrocardiography patch according to claim 1, further comprising:
   an SpO2 sensor provided on the backing.

9. An electrocardiography monitor, comprising:
   a backing comprising an elongated strip with a midsection connecting two rounded ends, wherein the midsection tapers in from each of the rounded ends and is narrower than each of the two rounded ends;
   a pair of electrodes, each electrode positioned on one of the rounded ends of the backing on a contact surface to capture electrocardiographic signals;
   a flex circuit coupled to each of the electrodes;
   a non-conductive receptacle affixed to the backing, the non-conductive receptacle comprising:
      electrical contacts, wherein the electrical contacts are provided on a surface of the non-conductive receptacle opposite the backing;
      a compartment; and
      a battery disposed within the compartment;
   a processor powered by the battery to write the electrocardiographic signals into memory; and
   a housing configured to engage the non-conductive receptacle.

10. The electrocardiography monitor according to claim 9, further comprising at least one of:
   a retention catch formed on the non-conductive receptacle; and
   a tension clip formed on the non-conductive receptacle.

11. The electrocardiography monitor according to claim 9, wherein the battery is one of rechargeable, replaceable, and disposable.

12. The electrocardiography monitor according to claim 9, further comprising:
   adhesive coating at least a portion of the contact surface of the backing.

13. The electrocardiography monitor according to claim 12, wherein the adhesive coats the two rounded ends of the backing on the contact surface.

14. The electrocardiography monitor according to claim 9, wherein the adhesive comprises hydrocolloid.

15. The electrocardiography monitor according to claim 11, wherein the two rounded ends of the backing are different shapes.

16. The electrocardiography monitor according to claim 9, wherein the backing extends beyond the flex circuit.

17. The electrocardiography monitor according to claim 9, further comprising:
   an SpO2 sensor provided on the backing.

* * * * *